(12) United States Patent
LoPachin et al.

(10) Patent No.: US 10,104,882 B2
(45) Date of Patent: Oct. 23, 2018

(54) METHODS AND COMPOSITIONS FOR PREVENTING AND TREATING ELECTROPHILE-MEDIATED TOXICITIES

(71) Applicant: MONTEFIORE MEDICAL CENTER, Bronx, NY (US)

(72) Inventors: Richard M. LoPachin, New Rochelle, NY (US); Terrence Gavin, New Paltz, NY (US)

(73) Assignee: Montefiore Medical Center, Bronx, NY (US)

( * ) Notice: Subject to any disclaimer, the term of this patent is extended or adjusted under 35 U.S.C. 154(b) by 0 days.

(21) Appl. No.: 14/785,861

(22) PCT Filed: Apr. 28, 2014

(86) PCT No.: PCT/US2014/035599
§ 371 (c)(1),
(2) Date: Oct. 21, 2015

(87) PCT Pub. No.: WO2014/179187
PCT Pub. Date: Nov. 6, 2014

(65) Prior Publication Data
US 2016/0074339 A1    Mar. 17, 2016

Related U.S. Application Data

(60) Provisional application No. 61/816,994, filed on Apr. 29, 2013.

(51) Int. Cl.
*A61K 31/122*    (2006.01)
*A01N 1/02*    (2006.01)
(Continued)

(52) U.S. Cl.
CPC ............ *A01N 1/0226* (2013.01); *A61K 31/05* (2013.01); *A61K 31/121* (2013.01);
(Continued)

(58) Field of Classification Search
None
See application file for complete search history.

(56) References Cited

U.S. PATENT DOCUMENTS

| 8,835,510 B2 | 9/2014 | LoPachin et al. |
| 2006/0008544 A1 | 1/2006 | Myhill et al. |

(Continued)

FOREIGN PATENT DOCUMENTS

| WO | 199002724 A1 | 3/1990 | |
| WO | 2011156181 A1 | 12/2011 | |
| WO | WO 2011156181 A1 * | 12/2011 | ........... A61K 31/055 |

OTHER PUBLICATIONS

Masutani, H., Oxidative stress and redox imbalance in acetaminophen toxicity, The Pharmacogenomics Journal, 1 (2001) pp. 165-166; accessed Apr. 4, 2017.*

(Continued)

*Primary Examiner* — Bethany P Barham
*Assistant Examiner* — Dominic Lazaro
(74) *Attorney, Agent, or Firm* — Amster, Rothstein & Ebenstein LLP

(57) ABSTRACT

Methods and compositions using 1,3-dicarbonyl compounds are disclosed for treating toxicity due to therapeutic agents and agents that causes oxidative cellular damage and for treating liver ischemia-reperfusion injury, as well as diseases and disorders that are improved through administration of N-acetylcysteine.

10 Claims, 11 Drawing Sheets

A. Enolization

B. Enolate formation

(51) Int. Cl.

| | |
|---|---|
| A61K 31/121 | (2006.01) |
| A61K 45/06 | (2006.01) |
| A61K 31/05 | (2006.01) |
| A61K 31/167 | (2006.01) |
| A61K 31/196 | (2006.01) |
| A61K 31/20 | (2006.01) |
| A61K 31/341 | (2006.01) |
| A61K 31/365 | (2006.01) |
| A61K 31/366 | (2006.01) |
| A61K 31/381 | (2006.01) |
| A61K 31/4015 | (2006.01) |
| A61K 31/4365 | (2006.01) |
| A61K 31/4439 | (2006.01) |
| A61K 31/675 | (2006.01) |
| A61K 33/24 | (2006.01) |

(52) U.S. Cl.
CPC .......... *A61K 31/122* (2013.01); *A61K 31/167* (2013.01); *A61K 31/196* (2013.01); *A61K 31/20* (2013.01); *A61K 31/341* (2013.01); *A61K 31/365* (2013.01); *A61K 31/366* (2013.01); *A61K 31/381* (2013.01); *A61K 31/4015* (2013.01); *A61K 31/4365* (2013.01); *A61K 31/4439* (2013.01); *A61K 31/675* (2013.01); *A61K 33/24* (2013.01); *A61K 45/06* (2013.01)

(56) References Cited

U.S. PATENT DOCUMENTS

| | | |
|---|---|---|
| 2006/0148908 A1 | 7/2006 | Park et al. |
| 2008/0139654 A1* | 6/2008 | Soderling ............... A61K 9/20 514/562 |
| 2008/0187901 A1 | 8/2008 | Doorschodt et al. |

OTHER PUBLICATIONS

Schafer, S., et al., Failure is an option: learning from unsuccessful proof-of-conjcept trials, Drug Discovery Today 2008, 13 (21/22), pp. 913-916.*
Cannon, J. G., Chapter Nineteen in Burger's Medicinal Chemistry and Drug Discovery, Fifth Edition, vol. I: Principles and Practice, Wiley-Interscience 1995, pp. 783-802, 784.*
Hung, H.L., & Nelson, S., Acetaminophen, Tintinalli's Emergency Medicine: A comprehensive Study guide, Feb. 15, 2015; accessed Apr. 5, 2017.*
PCT International Search Report and Written Opinion, dated Aug. 27, 2014 in connection with PCT International Application No. PCT/US2014/35599, 10 pages.
Yousef M I et al., entitled "Potential protective effects of quercetin and curcumin on paracetamol-induced histological changes, oxidative stress, impaired liver and kidney functions and haematotoxicity," Food and Chemical Toxicology, 48 (2010) 3246-3261.
Geohagen, B C et al., entitled "Enolate-Forming Phloretin Pharmacophores: Hepatoprotection in an Experimantal Model of Drug-Induced Toxicity," J Pharmacol Exp Ther 357;476-486, Jun. 2016.
LoPachin R M et al., entitled "Enolate-Forming Compounds as a Novel Approach to Cytoprotection," Chem. Res. Toxicol., 29, 2016, 2096-2107.
Zhang L et al., entitled "Protective Properties of 2-Acetylcyclopentanone in a Mouse Model of Acetaminophen Hepatotoxicity," J Pharmacol Exp Ther 346:259-269, Aug. 2013.
Chan K et al., entitled "An important function of Nrf2 in combating oxidative stress: Detoxification of acetaminophen," PNAS, Apr. 10, 2001, vol. 98, No. 8, 4611-4616.
Burke A S et al., entitled "Reactive Nitrogen Species in Acetaminophen-Induced Mitochondrial Damage and Toxicity in Mouse Hepatocytes," Chem. Res. Toxicol., 2010, 23, 1286-1292.
Fink M P, entitled "Ethyl pyruvate: a novel anti-inflammatory agent," Journal of Internal Medicine, 2007, 261; 349-362.
Gibson J D et al., entitled "Mechanism of Acetaminophen-Induced Hepatotoxicity: Covalent Binding versus Oxidative Stress," Chem. Res. Toxicol, 1996, 9, 580-585.
Hinson J A et al., entitled "Acetaminophen-Induced Hepatotoxicity: Role of Metabolic Activation, Reactive Oxygen/Nitrogen Species, and Mitochondrial Permeability Transition," Drug Metabolism Reviews, vol. 36, Nos. 3 & 4, pp. 805-822, 2004.
Hinson J A et al., entitled "Mechanisms of Acetaminophen-Induced Liver Necrosis," Adverse Drug Reactions, Handbook of Experimental Pharmacology, 196, 369-405, 2010.
Kosharskyy B et al., entitled "2-Acetylcyclopentanone, an Enolate-Forming 1, 3-Dicarbonyl Compound, Is Cytoprotective in Warm Ischemia-Reperfusion Injury of Rat Liver," J Pharmacol Exp Ther 353:150-158, Apr. 2015.
Lauterburg B H et al., entitled "Mechanism of Action of N-Acetylcysteine in the Protection Against the Hepatotoxicity of Acetaminophen in Rats In Vivo." J. Clin. Invest., vol. 71, Apr. 1983, 980-991.
Massey T E et al., entitled "Effects of N-Acetylcysteine on Metabolism, Covalent Binding, and Toxicity of Acetaminophen in Isolated Mouse Hepatocytes," Toxicology and Applied Pharmacology 60, 220-228 (1981).
Reid A B et al., entitled "Mechanisms of Acetaminophen-Induced Hepatotoxicity: Role of Oxidative Stress and Mitochondrial Permeability Transition in Freshly Isolated Mouse Hepatocytes," The Journal of Pharmacology and Experimental Therapeutics, vol. 312, No. 2, 509-516, 2005.
Samuni Y et al., entitled "The chemistry and biological activities of N-Acetylcysteine," Biochimica et Biophysica Acta, 1830 (2013) 4117-4129.
Smilkstein M J et al., entitled "Efficacy of Oral N-acetylcysteine in the Treatment of Acetaminophen Overdose," The New England Journal of Medicine, vol. 319. No. 24, Dec. 15, 1988, 1557-1562.
Zwingmann C et al. entitled "Metabolic Insights into the Hepatoprotective Role of N-Acetylcysteine in Mouse Liver," Hepatology, 2006; 43:454-463.

* cited by examiner

AcAc

2-ACP

2-ACH

A. Enolization

B. Enolate formation

METHODS AND COMPOSITIONS FOR PREVENTING AND TREATING ELECTROPHILE-MEDIATED TOXICITIES

CROSS-REFERENCE TO RELATED APPLICATIONS

This application is a U.S. national stage entry under 35 U.S.C. § 371 of PCT International Patent Application No. PCT/US2014/035599, filed on Apr. 28, 2014, which claims the benefit of U.S. Provisional Application No. 61/816,994, filed Apr. 29, 2013, the contents of each of which are hereby incorporated by reference.

STATEMENT OF GOVERNMENT SUPPORT

This invention was made with government support under grant number ES003830 awarded by the National Institutes of Health. The government has certain rights in the invention.

BACKGROUND OF THE INVENTION

Throughout this application various publications are referred to in superscript. Full citations for these references may be found at the end of the specification. The disclosures of these publications are hereby incorporated by reference in their entirety into the subject application to more fully describe the art to which the subject invention pertains.

Many pharmacotherapeutic compounds or their metabolites are electron-deficient species (electrophiles) that cause toxicity through chemical modification of functionally important proteins. For example, although at therapeutic doses, acetaminophen (paracetamol, N-acetyl-p-aminophenol; AAP) is a safe and effective antipyretic/analgesic, AAP overdose produces severe hepatotoxicity in humans and laboratory animals characterized by centrilobular necrosis. In the U.S., AAP overdose is the leading cause of drug-induced liver failure requiring transplantation[67].

The present invention addresses the need for improved methods and compositions for treating and preventing toxicity that can be associated with administration of therapeutic agents or agents that cause oxidative cellular damage to subjects.

SUMMARY OF THE INVENTION

The present invention provides methods of preventing or treating toxicity due to a therapeutic agent or an agent that causes oxidative cellular damage in a subject receiving the agent comprising administering to the subject a compound of formula (I) as described herein in an amount effective to prevent or reduce toxicity due to the agent.

The invention also provides methods of treating a disease or disorder that is improved through administration of N-acetylcysteine to a subject, the method comprising administering to the subject a compound of formula (I) in an amount effective to improve a sign or symptom of the disease or disorder.

The invention further provides methods of preventing or treating liver ischemia-reperfusion injury in a subject comprising administering to the subject a compound of formula (I) in an amount effective to prevent or reduce liver ischemia-reperfusion injury.

The invention further provides methods of increasing the viability of an organ for organ transplantation comprising adding to an organ preservation solution a compound of formula (I) in an amount effective to increase the viability of an organ for transplantation.

The invention also provides organ preservation solutions comprising a compound of formula (I) in an amount effective to increase the viability of an organ for transplantation.

The invention further provides compositions for preventing and treating toxicity due to a therapeutic agent comprising the therapeutic agent and a compound of formula (I) in an amount effective to prevent or reduce toxicity due to the agent.

DETAILED DESCRIPTION OF THE INVENTION

Figure 1:
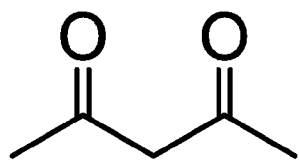
FIG. 1. Structures of acetylacetone (AcAc), 2-acetylcyclopentanone (2-ACP), and 2-acetylcyclohexanone (2-ACH).
Figure 1:
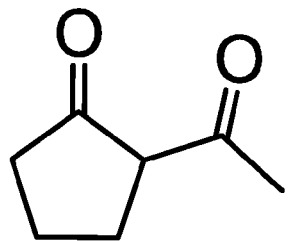
Figure 1:
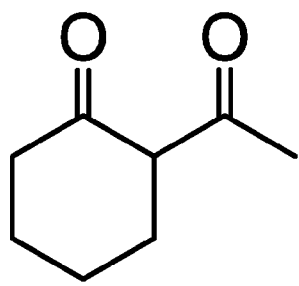

The present invention provides a method of preventing or treating toxicity due to a therapeutic agent or an agent that causes oxidative cellular damage in a subject receiving the agent comprising administering to the subject a compound of formula (I) in an amount effective to prevent or reduce toxicity due to the agent, wherein the compound has the structure:

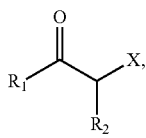

wherein $R_1$ and $R_2$ are independently H, alkyl, alkoxy alkyl, acyloxy alkyl, aryl, aryloxy, acyloxy aryl, cyclic, polycyclic, heterocyclic, heteroaryl, heteroaryloxy, or acyloxy heteroaryl; X is $COR_3$, $C(OR_4)(OR_5)R_3$, $C(SR_4)(SR_5)R_3$, $CO_2R_3$, $NO_2$, CN, $CON(R_3)_2$, $P(R_3)_3$, $P(OR_3)_3$, or $SO_2R_3$; $R_3$, $R_4$ and $R_5$ are independently H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —$CH_3$, —$NH_2$, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

Examples of such therapeutic agents include, but are not limited to, acetaminophen, diclofenac, cyclophosphamide, valproic acid, clopidogrel, esomeprazole, platinum containing antineoplastic agents such as cisplatin, and radiation used in radiation therapy. Examples of agents that can cause oxidative cellular damage include, but are not limited to, tobacco smoke, alcohol such as ethanol, and radiocontrast agents.

Preferably, the agent is a polarizable electrophile.

The toxicity caused by the agent can be hepatotoxicity, such as acetaminophen-induced hepatotoxicity, neurotoxicity, such as cisplatin-induced neurotoxicity, or any toxicity due to oxidative cellular stress.

The invention also provides a method of treating a disease or disorder that is improved through administration of N-acetylcysteine to a subject, the method comprising administering to the subject a compound of formula (I) in an amount effective to improve a sign or symptom of the disease or disorder, wherein the compound has the structure:

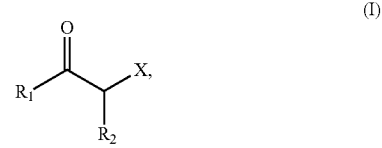

wherein $R_1$ and $R_2$ are independently H, alkyl, alkoxy alkyl, acyloxy alkyl, aryl, aryloxy, acyloxy aryl, cyclic, polycyclic, heterocyclic, heteroaryl, heteroaryloxy, or acyloxy heteroaryl; X is $COR_3$, $C(OR_4)(OR_5)R_3$, $C(SR_4)(SR_5)R_3$, $CO_2R_3$, $NO_2$, CN, $CON(R_3)_2$, $P(R_3)_3$, $P(OR_3)_3$, or $SO_2R_3$; $R_3$, $R_4$ and $R_5$ are independently H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —$CH_3$, —$NH_2$, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

Examples of such diseases or disorders include, but are not limited to, viral infections, such as human immunodeficiency virus infection/acquired immunodeficiency syndrome (HIV/AIDS) and influenza, pulmonary diseases, such as cystic fibrosis and chronic obstructive pulmonary disease (COPD), and emotional disorders, such as obsessive-compulsive syndrome and trichotillomania.

Signs and symptoms of various diseases and disorders are well known to those skilled in the art. Signs and symptoms of HIV/AIDS include, but are not limited to, fever, large tender lymph nodes, throat inflammation, rash, headache, sores of the mouth and genitals, neurological symptoms of peripheral neuropathy, pneumocystis pneumonia, HIV wasting syndrome, esophageal candidiasis, and recurring respiratory tract infections. Signs and symptoms of influenza include, but are not limited to, chills, fever, runny nose, sore throat, muscle pains, headache, coughing, and weakness and fatigue. Signs and symptoms of cystic fibrosis include, but are not limited to, difficulty breathing. Signs and symptoms of chronic obstructive pulmonary disease include, but are not limited to, shortness of breath. Signs and symptoms of obsessive-compulsive syndrome include, but are not limited to, uneasiness, apprehension, fear or worry, repetitive behaviors, excessive washing or cleaning, and nervous rituals. Signs and symptoms of trichotillomania include, but are not limited to, pulling out and eating one's own hair.

The invention further provides a method of increasing the viability of an organ for organ transplantation comprising adding to an organ preservation solution a compound of formula (I) in an amount effective to increase the viability of an organ for transplantation, wherein the compound has the structure:

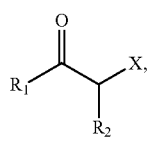

(I)

wherein $R_1$ and $R_2$ are independently H, alkyl, alkoxy alkyl, acyloxy alkyl, aryl, aryloxy, acyloxy aryl, cyclic, polycyclic, heterocyclic, heteroaryl, heteroaryloxy, or acyloxy heteroaryl; X is $COR_3$, $C(OR_4)(OR_5)R_3$, $C(SR_4)(SR_5)R_3$, $CO_2R_3$, $NO_2$, CN, $CON(R_3)_2$, $P(R_3)_3$, $P(OR_3)_3$, or $SO_2R_3$; $R_3$, $R_4$ and $R_5$ are independently H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —$CH_3$, —$NH_2$, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

Examples of organ preservation solutions include, but are not limited to, the University of Wisconsin (UW) solution and Leeds and histidine-tryptophan-ketoglutarate (HTK) solution.

The invention also provides an organ preservation solution comprising a compound of formula (I) in an amount effective to increase the viability of an organ for transplantation, wherein the compound has the structure:

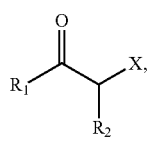

(I)

wherein $R_1$ and $R_2$ are independently H, alkyl, alkoxy alkyl, acyloxy alkyl, aryl, aryloxy, acyloxy aryl, cyclic, polycyclic, heterocyclic, heteroaryl, heteroaryloxy, or acyloxy heteroaryl; X is $COR_3$, $C(OR_4)(OR_5)R_3$, $C(SR_4)(SR_5)R_3$, $CO_2R_3$, $NO_2$, CN, $CON(R_3)_2$, $P(R_3)_3$, $P(OR_3)_3$, or $SO_2R_3$; $R_3$, $R_4$ and $R_5$ are independently H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —$CH_3$, —$NH_2$, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

The invention further provides a composition for preventing and treating toxicity due to a therapeutic agent comprising the therapeutic agent and a compound of formula (I) in an amount effective to prevent or reduce toxicity due to the agent, wherein the compound has the structure:

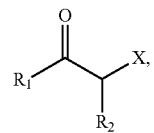

(I)

wherein $R_1$ and $R_2$ are independently H, alkyl, alkoxy alkyl, acyloxy alkyl, aryl, aryloxy, acyloxy aryl, cyclic, polycyclic, heterocyclic, heteroaryl, heteroaryloxy, or acyloxy heteroaryl; X is $COR_3$, $C(OR_4)(OR_5)R_3$, $C(SR_4)(SR_5)R_3$, $CO_2R_3$, $NO_2$, CN, $CON(R_3)_2$, $P(R_3)_3$, $P(OR_3)_3$, or $SO_2R_3$; $R_3$, $R_4$ and $R_5$ are independently H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —$CH_3$, —$NH_2$, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

Examples of therapeutic agents include, but are not limited to, acetaminophen, diclofenac, cyclophosphamide, valproic acid, clopidogrel, and esomeprazole. Preferably, the therapeutic agent is a polarizable electrophile. Preferably, for oral administration, the composition is formulated with an enteric coating.

The toxicity can be, for example, hepatotoxicity, neurotoxicity, or toxicity due to oxidative cellular stress.

The invention also provides a method of preventing or treating liver ischemia-reperfusion injury in a subject comprising administering to the subject a compound of formula (I) in an amount effective to prevent or reduce liver ischemia-reperfusion injury, wherein the compound has the structure:

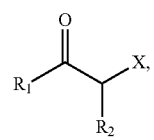

(I)

wherein $R_1$ and $R_2$ are independently H, alkyl, alkoxy alkyl, acyloxy alkyl, aryl, aryloxy, acyloxy aryl, cyclic, polycyclic, heterocyclic, heteroaryl, heteroaryloxy, or acyloxy heteroaryl; X is $COR_3$, $C(OR_4)(OR_5)R_3$, $C(SR_4)(SR_5)R_3$, $CO_2R_3$, $NO_2$, CN, $CON(R_3)_2$, $P(R_3)_3$, $P(OR_3)_3$, or $SO_2R_3$; $R_3$, $R_4$ and $R_5$ are independently H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —CH3, —NH2, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

The subject can be at risk for liver ischemia-reperfusion injury, for example, because the subject is undergoing removal of at least part of the liver or because the subject is undergoing liver transplantation. Alternatively, the subject can have, for example, a disease that reduces blood flow to the liver, such as, e.g., stroke or coronary artery occlusion. Preferably, administration of the compound of formula (I) to the subject is effective to reduce elevated serum levels of one or more of alanine aminotransferase (ALT), aspartate aminotransferase (AST) and lactate dehydrogenase (LDH).

In any of the compounds used in any of the methods disclosed herein or in any of the solutions or compositions disclosed herein, any ring formed between $R_2$ with $R_1$ and/or $R_3$ can be independently a 4-12 member ring, for example, a 5-6 member ring. Furthermore, any ring formed between $R_2$ with $R_1$ and/or $R_3$ can independently contain one or more O, S, N or substituted N, where substitution at N is any alkyl or acyl group.

In any of the compounds used in any of the methods disclosed herein or in any of the solutions or compositions disclosed herein, any alkyl can be independently C1-C6 alkyl, for example, C1-C3 alkyl.

Examples of compounds include those having the structure:

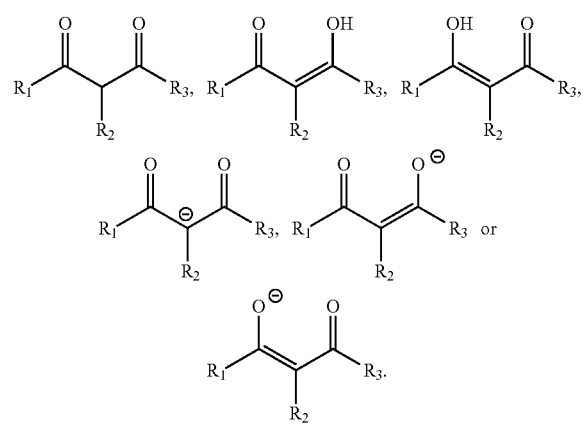

Additional examples of compounds include those having the structure:

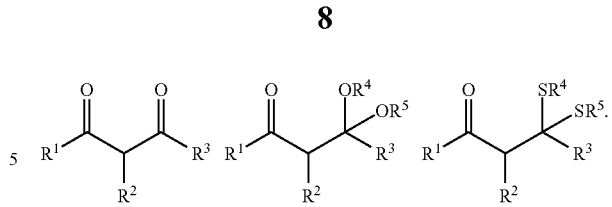

Preferred compounds include those having the structure:

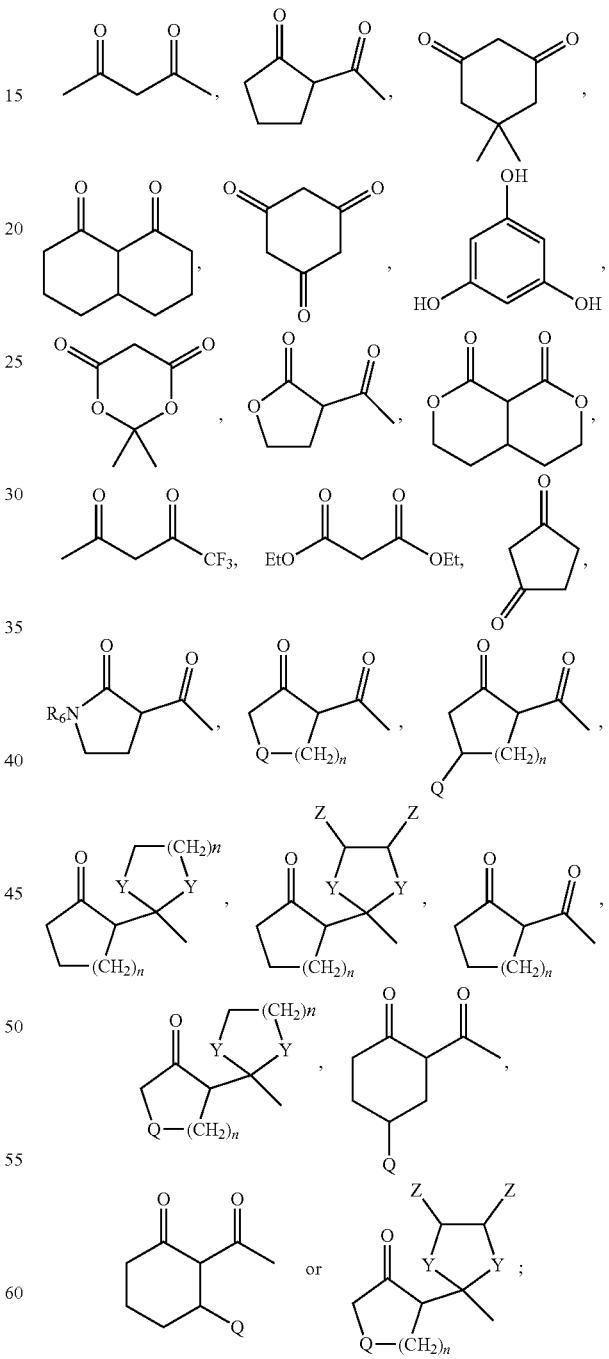

wherein $R_6$=H, alkyl, alkoxy, acyloxy, aryl or acyloxyaryl; or a tautomer thereof; n=1-3; Q is O, S, $NCOR_1$, $NCO_2R_1$, or $NR_1R_2$; Y is O, S or Se; and Z is $OR_1$ or $SR_1$.

More preferred compounds include

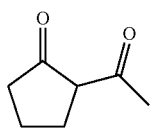

or a tautomer thereof.

Pharmaceutically acceptable salts that can be used include non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The compounds can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intranasal administration, and administration through an osmotic mini-pump.

When the compound or composition is administered by oral administration, the compound or composition is preferably formulated with an enteric coating. Enteric coatings are well known in the art. The enteric coating can be stable at the acidic pH found in the stomach, but can break down in the alkaline environment of the small intestine. Materials used for enteric coatings include fatty acids, waxes and plant fibers.

The compounds can be applied to the skin, for example, in compositions formulated as skin creams, or as sustained release formulations or patches.

The compound can be administered to the subject at the same time that the agent is administered to the subject. In a preferred embodiment, the compound and the therapeutic agent are administered in the same formulation. In other embodiments, the compound is administered to the subject before and/or after the agent is administered to the subject.

The compound can be administered to a subject known to be at risk for liver ischemia-reperfusion injury before the onset of the ischemia, for example, before or at the start of a surgical procedure. The compound can also be administered to a subject during liver ischemia-reperfusion or as soon as possible after liver ischemia-reperfusion.

The invention also provides for the use of a compound of formula (I) for preventing or treating toxicity due to a therapeutic agent or an agent that causes oxidative cellular damage in a subject. The invention further provides for the use of a compound of formula (I) for treating a disease or disorder that is improved through administration of N-acetylcysteine to a subject.

Analogue 1,3-dicarbonyl compounds that cannot be purchased commercially (e.g., Aldrich) are prepared by treating enamines (formed by reaction of the parent ketone with pyrrolidine or morpholine) with acetic anhydride (or trifluoroacetic anhydride). The resulting iminium salts are hydrolyzed in boiling water. 1,3-Dicarbonyl compounds can be selectively acetalized (or thioacetalized) using heteropoly acids such as $H_3PW_{12}O_{40}$ (tungstophosphoric acid) as catalysts[93].

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Figure 2A:
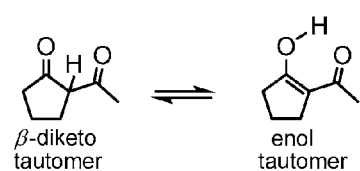
FIG. 2A-2B. (A) Schematic diagram showing that 2-ACP exists as equilibrating tautomers with the enol-containing isomers generally predominating. (B) Schematic diagram showing that, loss of a proton from either the central ("α") carbon in the diketo tautomer of 2-ACP or the enol hydroxyl group of the isomer yields a nucleophilic enolate ion.
Figure 2B:
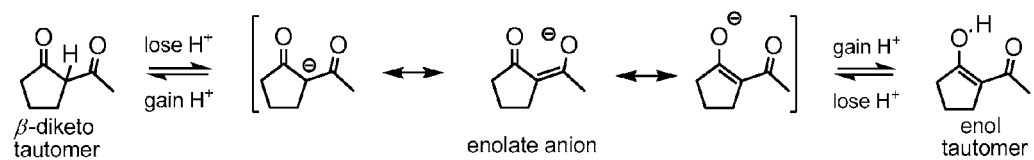

Many pharmacotherapeutic compounds or their bio-activated metabolites are electron-deficient species (electrophiles) that cause toxicity through chemical modification of functionally important proteins. Since such modifications generally involve covalent adduct formation at nucleophilic amino acid side chain residues on the proteins (e.g., cysteine, histidine;[23,80,84]), compounds that function as surrogate nucleophilic targets are likely to be cytoprotective. A series of 1,3-dicarbonyl compounds (FIG. 1) has been identified as primary candidates in this regard. These β-diketones exist as a mixture of equilibrating keto-enol tautomers in which the enol isomer normally predominates (FIG. 2A). Their nucleophilicity stems from the ability of these compounds to ionize in physiological buffer solutions. For example, 2-acetylcyclopentanone (2-ACP) is relatively acidic (pKa=7.8) and will, upon ionization, yield a resonance stabilized carbanionic enolate (FIG. 2B) that can scavenge chemical electrophiles via adduct formation. In addition, enolates with conformational flexibility (like those in FIG. 1) can form bi-dentate chelation complexes with cationic metal ions. Accordingly, research has shown that these compounds provide protection in experimental models of toxicity induced by either electrophiles or oxidative stress[54,91]. The predictable chemical behavior of enolates formed from 2-ACP and other 1,3-dicarbonyl compounds should, therefore, render them useful in treating drug-induced toxicities that involve electrophiles; e.g., cisplatin neurotoxicity, acetaminophen hepatotoxicity. Although the idea that dicarbonyl compounds are cytoprotective is unprecedented, it is based on the recognition that curcumin, phloretin and other plant-derived polyphenolic compounds (phytopolyphenols) also exhibit ionizable dicarbonyl moieties that appear to be responsible for their well-documented therapeutic properties[2,6,54,89]. However, certain properties of these polyphenols limit clinical utility; i.e., chemical instability, significant toxicity and poor bioavailability[7,26,27,88]. The 1,3-dicarbonyl compounds lack these negative characteristics and therefore represent a rational platform for safe and efficacious cytoprotectants with broad therapeutic applications.

The present application describes key research advances that justify claims regarding therapeutic applications of these compounds. In particular, data are presented indicating that the present invention can completely prevent acetaminophen (AAP or APAP) toxicity in a mouse model. This finding not only has substantial implications for emergency medicine, but could signify the very broad therapeutic applicability of the invention to other drug-induced toxicities and pathogenic processes mediated by electrophile-induced oxidative stress. In the sections to follow, electrophile-based toxicity and potential mechanisms of cytoprotection are discussed. This information will provide a logical framework for subsequent discussions of the 1,3-dicarbonyl enolates and their usefulness in electrophile mediated diseases and toxic conditions.

Electrophiles as Toxic Mediators

Electrophiles are electron-deficient species that can form covalent bonds with electron-rich nucleophiles. It is now recognized that most toxicants are electrophiles that cause cell damage by reacting with nucleophilic targets on biological macromolecules[12,30,45-49,52,66,77,78]. Electrophilic toxicants do not, however, react arbitrarily with nucleophiles, and instead, these interactions exhibit a significant degree of selectivity as predicted by the Hard and Soft, Acids and Bases (HSAB) theory. Thus, electrophiles and nucleophiles are classified as being either soft (polarizable) or hard (non-polarizable) and, based on HSAB principles, toxic electrophiles will react preferentially with nucleophilic biological targets of comparable softness or hardness (reviewed in LoPachin et al.[54-56]). The 1,3-dicarbonyl compounds are soft nucleophiles (see below) that form covalent adducts with (scavenge) soft electrophiles, which includes industrial pollutants (e.g., acrolein, acrylamide, methyl vinyl ketone), drug metabolites (e.g., NAPQI, N-acetyl-p-benzoquinone imine, a metabolite of acetaminophen) and dietary contaminants (e.g., acrylamide). Soft electrophiles also play a prominent role in cellular oxidative stress, which is a pathogenic feature of many diseases (e.g., atherosclerosis, diabetes, Alzheimer's disease) and tissue injury states (e.g., spinal cord trauma). Specifically, the excessive fragmentation of polyunsaturated fatty acids that occurs during oxidative stress results from the generation of lipid peroxides that undergo chain cleavage to yield α,β-unsaturated aldehydes such as acrolein and 4-hydroxy-2-nonenal (HNE)[29,38,43,50,52,76]. These and other soft electrophiles will preferentially form 1,4-Michael adducts with soft anionic sulfhydryl thiolates on cysteine residues of proteins. In contrast, although certain nitrogen atoms (e.g., N-7 atoms on guanine bases of DNA or side-chain amino groups on lysine and histidine residues) are also nucleophilic, these are harder sites and are, therefore, less favorable targets for acrolein and other soft electrophiles[55,69,85]. Considerable evidence now indicates that soft electrophiles cause toxicity by forming adducts with soft nucleophilic sulfhydryl thiolate sites that regulate the activities of functionally critical cellular proteins[12,41,48,51,69]. It is therefore clear that 1,3-dicaronyl compounds can provide cytoprotection by acting as surrogate soft nucleophilic targets for toxic soft electrophiles (see below).

Enolate Therapy: A New Pharmacological Approach to Cytoprotection

The idea that the 1,3-dicarbonyl compounds can be cytoprotective stems from the recognition that the central heptadienone bridge of curcumin is also a dicarbonyl compound and that the presence of this substructure is critically important for cytoprotection[6,54,89]. AcAc, 2-ACP and related analogues are non-phenolic enolate-forming (FIG. 1) 1,3-dicarbonyl compounds and, like curcumin, these chemicals exist in biological solutions as equilibrating tautomers (FIG. 2A) with the enol-containing isomer in excess. In each case, ionization (FIG. 2B) yields a nucleophilic anionic enolate[54]. Based on this, it was theorized that structurally related β-dicarbonyl compounds could act as cytoprotectants and, indeed, a series of 1,3-dicarbonyl compounds are highly protective in cell culture and animal models of oxidative stress[54,91]. That this protection occurred through formation of 1,4-Michael adducts with soft electrophiles[54] is indicated by the fact that Michael addition was originally designated as the conjugate addition of an enolate ion to an α,β-unsaturated carbonyl derivative[9,57]. In addition, metal ion chelation is likely involved since this is a well known characteristic of the nucleophilic AcAc enolate[54,55]. In support of these mechanisms, studies[54] demonstrated that, although the 1,3-dicarbonyls do not scavenge free radicals, these compounds can form adducts with acrolein and can chelate metal ions. Thus, the 1,3-dicarbonyl compounds, like the dietary polyphenols, undergo at least two chemical interactions (metal chelation and aldehyde adduction) that have broad cytoprotective implications. Unlike the phytopolyphenols, however, the 1,3-dicarbonyl compounds (FIG. 1) are simple, chemically stable compounds that are relatively water soluble, rapidly absorbed and bioavailable as indicated by their large volume of distribution[5]. Furthermore, the acute toxicity of these chemicals is low ($LD_{50}$>800 mg/kg) and longitudinal dosing studies indicate a low incidence of systemic toxicity (e.g., 400-600 mg/kg/d×60 d)[5,20,83]. Perhaps most importantly, HSAB parameters derived from quantum mechanical calculations indicate that the nucleophilic reactivity of enolates generated from 2-ACP, AcAc and related analogs is considerably higher than that of the curcumin enolate (nucleophilicity $\omega^-$; Table 1). This indicates that the cytoprotective efficacy of the 1,3-dicarbonyl compounds could be substantial.

Theoretical Determination of Enolate Nucleophilicity

The designation of "hard" or "soft" is based on the inherent electronic characteristics of a specified chemical structure and can be determined from orbital energies obtained by using quantum mechanical models. Once computed the energies of the respective frontier molecular orbitals; i.e., the Highest Occupied Molecular Qrbital ($E_{HOMO}$) and the Lowest Unoccupied Molecular Qrbital ($E_{LUMO}$) enable the calculation of HSAB parameters that can then be used to define the electrophilicity (co) and nucleophilicity ($\omega^-$)[11,36] of a chemical species. Application of these parameters has significantly increased understanding of electrophile and nucleophile behavior in various biological systems[55,77,78,85]. Accordingly, the $\omega^-$ algorithm was used to calculate the relative nucleophilicity of enolates formed from 1,3-dicarbonyl compounds using NAPQI as the electrophilic target (Table 1). It can be concluded that the enolate form is the relevant nucleophile (i.e., acrolein reacts with the enolate, rather than with the enol or keto isomers), since the $\omega^-$ values for the enol and keto isomers of all chemicals considered were substantially lower (ca. 100-fold, data not shown) than the respective enolate values. When other electrophile targets were applied in the co algorithm, the same relative enolate reactivity was evident although the absolute values increased (p-benzoquinone) or decreased (acrolein), depending on the potency of the electrophile (data not shown). Finally, it is noteworthy that the curcumin enolate is significantly less nucleophilic than the enolate forms of the other 1,3-dicarbonyl compounds (Table 1).

TABLE 1

HSAB and Ionization Parameters for Thiolate and Enolate Nucleophiles

| Nucleophile | σ (×10⁻³ ev⁻¹) | ω⁻ (×10⁻³ ev) | p$K_a$ | % Anion (pH = 7.4) |
|---|---|---|---|---|
| 2-ACP (enotate) | 418 | 485 | 7.8 | 28.5 |
| GSH (thiotate) | 427 | 548 | 8.6 | 5.9 |
| NAC (thiolate) | 367 | 667 | 9.5 | 0.8 |
| Curcumin (enolate) | 604 | 221 | 7.8 | 28.5 |

The $E_{LUMO}$ and $E_{HOMO}$ energies were derived from calculations of equilibrium geometries at ground state with DF B3-LYP 6-31G* in water starting from 6-31G* geometry using Spartan08 (version 1.0.3) software (Wavefunction Inc., Irvine CA). The nucleophilicity index (ω⁻) was calculated as ω⁻ = $\eta_A$ ($\mu_A - \mu_B$)²/2($\eta_A + \eta_B$)², where A = the selected enolate or thiolate and B = NAPQI. Global (whole molecule) softness (σ) was calculated as the inverse of hardness or σ = 1/η, where hardness (η) = ($E_{LUMO} - E_{HOMO}$)/2 and μ = ($E_{LUMO} + E_{HOMO}$)/2.

Abbreviations:
2-ACP = 2-acetylcyclopentanone;
GSH = glutathione;
NAC = N-acetylcysteine.

Adduct Kinetics of 1,3-Dicarbonyl Compounds

Initial in chemico and cell culture studies[54] determined that the enolate forming 1,3-dicarbonyl compounds could prevent electrophile-induced loss of protein and non-protein sulfhydryl groups. These experiments established an index of cytoprotection that was based on evidence that soft electrophiles, like acrolein, produced toxicity by forming Michael-type adducts with soft nucleophilic thiolate groups (anionic organo-sulfur moieties) on functionally critical proteins[24,49,53,69,90]. If the soft nucleophilic enolates of 1,3-dicarbonyl derivatives were cytoprotective through scavenging electrophiles, then these compounds would be expected to disrupt the adduct reaction between an electrophile and a corresponding nucleophilic target. Kinetic assays at physiological conditions (data not shown) revealed that the rate of sulfhydryl loss associated with acrolein incubation was slowed predictably by a series of 1,3-dicarbonyl compounds. 2-ACP completely prevented acrolein-induced thiol loss, whereas dimedone, (DMD), Meldrum's acid (MA) and acetylacetone (AcAc) substantially slowed the rate of thiol loss. Neither diethyl malonate (DEM; a β-diester) nor 2,5-hexanedione (HD), a γ or 1,4-diketone, affected the rate of sulfhydryl loss. To demonstrate that the formation of the enolate was dependent upon ionization, the thiol protection afforded by DEM, AcAc and 1,1,1-trifluoro-2,4-pentanedione (TFPD) was determined at pH 9.0. Thiol protection by AcAc (p$K_a$ 9.0) was virtually complete at the elevated pH level, whereas the ability of DEM (p$K_a$ 12.9) to slow acrolein-induced thiol loss was significantly increased. This pH-dependent effect reflects the increased enolate concentration of AcAc and DEM (e.g., raising the pH from 7 to 9 increases the relative enolate concentration of AcAc from 1% to 50% in solution). In contrast, the protective capacity of TFPD did not increase at the more basic pH, since at neutral conditions this 1,3-dicarbonyl analog already exists in the enolate-state (99%) due to its relatively high acidity (p$K_a$=4.7). Additional in chemico studies[54] demonstrated that, although the 1,3-dicarbonyl compounds did not scavenge free radicals, the conformational flexibility of 2-ACP and AcAc afforded these compounds significant ability to complex metal ions but MA, DMD and 1,3-cyclopenanedione (CPD) were inactive in this regard. These data indicated that certain structurally simple 1,3-dicarbonyl compounds shared with the phytopolyphenols the ability to scavenge soft electrophilic unsaturated carbonyl compounds through adduct formation at their nucleophilic enolate sites. As might be expected, however, the ability of these compounds to chelate metal ions requires that a specific conformation (presumably s-cis) be achievable.

Enolate Protection in Synaptosomal and Nerve Cell Culture Models

The preservation of thiols in the preceding kinetic studies strongly suggested that the 1,3-dicarbonyl derivatives had protective actions and, therefore, cytoprotection was evaluated in more complex biological models of oxidative stress; i.e., isolated CNS nerve terminals and nerve cells in culture. For comparative purposes, the analyses also included NAC as a representative soft thiol-type nucleophile. Rat striatal synaptosomes were prepared according to the methods of LoPachin et al.[54] and dopamine (DA) membrane transport was measured as an index of synaptosomal function. Isolated synaptosomes were exposed to graded concentrations of acrolein (1-1000 μM) alone or in combination with a putative cytoprotectant (500 μM). Results[54] showed that the enolates shifted the concentration-response curve to the right for acrolein-induced transport inhibition, which resulted in corresponding increases in the acrolein $IC_{50}$. Thus, 2-ACP produced the largest increases in the acrolein $IC_{50}$, whereas the changes induced by MA, DMD and NAC were more modest. TFPD and CPD were relatively ineffective and neither DEM nor HD significantly affected the acrolein $IC_{50}$. The rank order of synaptosomal function and thiol protection by the β-diketo analogs was equivalent to that defined in the preceding kinetic studies. This rank order reflects contributions from both the respective acid strengths of the 1,3-dicarbonyl derivatives (indicated by p$K_a$ values) and the relative nucleophilicity of the enolate (indicated by ω⁻). Such behavior is fully consistent with the second order kinetics expected for the Michael reaction; that is, Rate=k [Nucleophile][Electrophile]. Thus, for a given concentration of a specific electrophile, a lower p$K_a$ value for the dicarbonyl compound would increase the concentration of the enolate nucleophile and thereby increase the reaction rate. A greater nucleophilicity would enhance the rate constant (k), which would also increase the rate. Specifically, DMD, with a p$K_a$ value of 5.3, will exist primarily (99%) as the acrolein-scavenging anionic enolate at pH 7.4. Based on the significant nucleophilicity of this analog (ω⁻=174 vs. acrolein), it is not surprising that DMD is a powerful cytoprotectant. DEM is a better nucleophile versus acrolein (ω⁻=228) than DMD; however, it is not cytoprotective since its high p$K_a$ value (12.9) indicates very little enolate (<0.1%) is available at neutral pH. Although TFPD is a weaker nucleophile (ω⁻=99) than the other analogs, this derivative offers some thiol protection at pH 7.4 since it almost completely ionized (pKa=4.7). However, it should be noted that lower p$K_a$ values imply greater enolate stability and consequently, the use of strongly acidic dicarbonyl compounds should lead to a greater degree of reversibility in the Michael reaction (Equation 1). Thus, in order to balance kinetics with thermodynamic concerns, the best candidates for cytoprotection will combine high nucleophilicity (faster reactions) with appropriate acidity (increased enolate concentration and acceptable adduct stability).

enolate+electrophile⇌Michael adduct     Equation 1:

The demonstrated ability of the 1,3-dicarbonyl analogs to prevent acrolein-induced thiol loss suggests that the nucleophilic enolate of these chemicals could provide significant cytoprotection by scavenging electrophilic mediators of oxidative stress. As a more complex biological model, the relative abilities were determined of the 1,3-dicarbonyls to protect MN9D cells, a dopaminergic cell line, from acrolein or hydrogen peroxide ($H_2O_2$) induced cell death[54]. Exposure of cells to graded concentrations of acrolein (50-150 µM) caused cell death with an $LC_{50}$ of 96 µM ($LC_{50}$=acrolein concentration producing 50% cell lethality). Pre-incubation with 2-ACP or NAC completely prevented acrolein-induced cell loss, whereas AcAc and TFPD were moderately protective. As expected, neither DEM nor HD was effective. The relative abilities of the 1,3-dicarbonyl compounds to protect cells against $H_2O_2$ toxicity were also determined[54]. This system represents a more complete model of oxidative stress since the hydroxyl radical (formed from intracellular $H_2O_2$ during the Fenton reaction) mediates the generation of toxic aldehyde by-products such as acrolein and 4-hydroxy-2-nonenal (HNE). The data show that 2-ACP completely prevented cell death in this model, while AcAc and TFPD provided 3-fold protection against $H_2O_2$-induced cytotoxicity. In contrast, NAC was significantly less efficacious and both CPD and HD were ineffective.

The data discussed thus far indicate that nucleophilic enolates of β-dicarbonyl compounds act as surrogate targets for acrolein. The resulting electrophile sequestration prevented loss of sulfhydryl groups, which in turn preserved synaptosomal function and promoted neuronal cell survival. This has significant implications for cytoprotection because acrolein is one of several soft electrophilic α,β-unsaturated aldehyde end-products (e.g., 4-hydroxy-2-nonenal, 4-oxo-2-nonenal) generated during membrane lipid peroxidation. Evidence indicates that these aldehydes are specifically involved in mechanisms of cell injury associated with chronic diseases and acute tissue trauma. $H_2O_2$ cytotoxicity in cell culture is a more complex biological model since the observed injury is mediated by the sequential involvement of electron deficient species such as hydroxyl radicals, toxic aldehyde byproducts and transition metal ions that catalyze the Fenton reaction. Based on data from the acrolein injury models, aldehyde adduction is a likely mechanism of 1,3-dicarbonyl cytoprotection in $H_2O_2$-exposed cell cultures. In addition, studies have confirmed the metal chelating abilities of 2-ACP and AcAc. Accordingly, these structurally flexible 1,3-dicarbonyl compounds provided substantial cytoprotection in the $H_2O_2$ model. The compelling structure-activity relationship identified between conformationally flexible 1,3-dicarbonyl compounds and the amelioration of oxidative stress suggests that, although free radical trapping is not involved, metal ion chelation and the formation of Michael adducts with toxic unsaturated aldehydes are important components of 1,3-dicarbonyl cytoprotection. These compounds could, therefore, provide optimal protection during cellular oxidative stress by intersecting the pathophysiological process at multiple steps.

Enolate-Mediated Protection in Animal Models of Oxidative Stress

The preceding research indicates that 2-ACP, AcAc and several other 1,3-dicarbonyl enols can prevent cytotoxicity in several cell culture models of oxidative injury. Mechanistic studies show that this protection is mediated by scavenging soft electrophiles (e.g., unsaturated aldehydes) and by chelating metal ions (e.g., $Cu^{2+}$, $Fe^{2+}$) that participate in oxidative stress. Based on the success of this in vitro research, studies were initiated in a mouse model of acetaminophen poisoning. This is a well-described animal model of electrophile-induced oxidative stress that represents a relevant system for testing the cytoprotective efficacy of the 1,3-dicarbonyl compounds.

Acetaminophen Toxicity: Introduction

Although at therapeutic doses, acetaminophen (paracetamol, N-acetyl-p-aminophenol; AAP) is a safe and effective antipyretic/analgesic, AAP overdose produces severe hepatotoxicity in humans and laboratory animals characterized by centrilobular necrosis. In the US, AAP overdose is the leading cause of drug-induced liver failure requiring transplantation[67]. AAP is oxidized by liver cytochrome P-450 enzymes to the highly reactive N-acetyl-p-benzoquinone imine (NAPQI), which can subsequently decompose to an equally reactive product, p-benzoquinone (pBQ)[16,62]. Both NAPQI and pBQ are potent electrophiles and HSAB calculations (Table 2) indicate that these quinone derivatives are very soft (σ) and highly electrophilic (ω). As such, these toxicants will rapidly form covalent adducts with soft nucleophilic sulfhydryl groups[45,46,55]. Indeed, in chemico studies revealed a second order rate constant for the reaction of NAPQI with nucleophilic cysteine sulfhydryl groups ($3.2 \times 10^4$ $M^{-1}$ $s^{-1}$)[59] that is five orders of magnitude higher than the reaction rate of acrylamide with thiols[47].

TABLE 2

Electrophilicity Index (ω) and Softness (σ) of Selected Toxicants

| Electrophile | σ ($\times 10^{-3}$ $ev^{-1}$) | ω (ev) | Log $IC_{50}$ |
|---|---|---|---|
| NAPQI | 499 | 6.83 | 0.92 |
| pBQ | 524 | 7.78 | 1.06 |
| tBQ | 505 | 7.20 | 1.24 |
| NEM | 410 | 5.10 | 1.23 |
| Acrolein | 371 | 3.82 | 1.72 |
| Acrylamide | 346 | 2.62 | 5.63 |

The $E_{LUMO}$ and $E_{HOMO}$ energies were derived from calculations of equilibrium geometries at ground state with DF B3-LYP 6-31G* in water starting from 6-31G* geometry using Spartan08 (version 1.0.3) software (Wavefunction Inc., Irvine CA). Global softness (σ) was calculated as the inverse of hardness (η), where $\eta = E_{LUMO} - E_{HOMO}/2$. The electrophilicity index (ω) was calculated as $\omega = \mu^2/2\eta$ (for details see Martyniuk et al.[60]). $IC_{50}$ value is the electrophile concentration that causes 50% loss of the GSH sulfhydryl group. These data indicate that softness and electrophilicity are significant determinants of toxic potency (respective $IC_{50}$ values; see LoPachin et al.[47,49,55]).
Abbreviations:
NAPQI = N-acetyl-p-benzoquinone imine;
pBQ = p-benzoquinone;
tBQ = tert-butylquinone;
NEM = N-ethylmaleimide.

NAPQI may inactivate hepatocyte proteins by rapidly forming Michael-type adducts with cysteine sulfhydryl groups[19,39,70] and could also deplete cellular GSH through electrophile conjugation or by oxidation of GSH to GSSG with concomitant reduction to AAP[1,71]. Considered together, this evidence indicates that NAPQI causes hepatotoxicity through adduct-mediated inactivation of hepatocyte proteins and through the oxidative consequences (e.g., lipid peroxidation) of cellular GSH depletion[31,33-35]. Thiol targeting of NAPQI formed the basis for early research[14,63,64] that ultimately demonstrated hepatoprotection afforded by thiol-containing compounds acting as surrogate nucleophile targets. This realization eventually led to the development of N-acetylcysteine (NAC) as the preferred antidote for treatment of AAP poisoning[32,81]. In this hepatoprotective role, NAC is presumed to act as a substrate for GSH synthesis and to scavenge NAPQI[14]. NAC administration is nonetheless associated with a number of adverse effects (e.g., nausea, vomiting, anaphylactoid reactions, myocardial toxicity) and with concerns regarding overall clinical efficacy[22,32,75]. Based on the results from the following comparative in chemico and in vivo data, administration of the otherwise bio-orthogonal 2-ACP (e.g., enolate therapy) represents a more rational approach to the management of acetaminophen poisoning and other conditions with a common molecular etiology of electrophile-induced oxidative stress.

Enolate Hepatoprotection in Acetaminophen Toxicity: In Chemico Studies

Previously published in chemico studies showed that 2-ACP and other 1,3-dicarbonyl compounds can significantly slow the rate of sulfhydryl loss induced by acrolein[54]. However, acrolein and other electrophiles used in this research are α,β-unsaturated carbonyls, whereas NAPQI and pBQ are quinone derivatives. As illustrated in Table 2, the quinones are softer and substantially more electrophilic chemicals than acrolein and the other type-2 alkenes. The high electrophilic reactivity of the quinones corresponds to the respective $IC_{50}$'s, which are significantly lower than the $IC_{50}$ for acrolein (displayed as logarithmic values, Table 2). Therefore, given these electronic differences, preliminary in chemico studies were conducted to determine the relative abilities of a 1,3-dicarbonyl series to prevent NAPQI concentration-dependent loss of GSH sulfhydryl groups (for methodological procedures see LoPachin et al.[54]). Results (FIG. 3) show that, at equimolar concentrations (50 μM), MA and DMD are ineffective at preventing NAPQI-induced thiol loss; i.e., compare the $IC_{50}$ value for NAPQI alone (9.1 μM) with corresponding NAPQI values in the presence of MA (9.7 μM) or DMD (10.4 μM). Although both compounds are relatively acidic (low $pK_a$ values), thiol protection is limited since the corresponding adduct reactions involving the enolates of these acids are likely to be reversible. CPD and AcAc provided minimal thiol protection in accordance with their relatively decreased ability to ionize (high $pK_a$ values) and consequentially, lower concentrations of the nucleophilic enolate at pH 7.4. Whereas NAC is a better nucleophile than 2-ACP (Table 1), only minimal protection was observed since the $pK_a$ value of this thiol is high and thus, less than 1% of the cysteine sulfhydryl group is in the nucleophilic thiolate state. However, 2-ACP significantly shifted the concentration curve to the right (FIG. 3) resulting in a three-fold increase in the respective $IC_{50}$ value (9.1 μM vs. 24.8 μM). Hence, although not as powerful a nucleophile as NAC (Table 1), the pKa of 2-ACP is lower and, therefore, at physiological pH almost 30% of this substance is present as the nucleophilic enolate. 2-ACP was the most protective 1,3-dicarbonyl compound tested in this and other studies[54] and was, therefore, the focus of subsequent research. FIG. 4 shows that 2-ACP provides thiol protection over a broad range of concentrations; i.e., 25-200 μM. 2-ACP (50 μM) was also effective at protecting thiol loss induced by pBQ, the degradation product of NAPQI (data not shown). Considered together, these data demonstrate that the 1,3-dicarbonyl compounds can readily scavenge NAPQI and pBQ and thereby prevent loss of sulfhydryl groups. These electrophiles target nucleophilic sulfhydryl groups that play critical roles in protein function and cellular redox balance.

Enolate Hepatoprotection in Acetaminophen Toxicity: Animal Studies.

Figure 3:
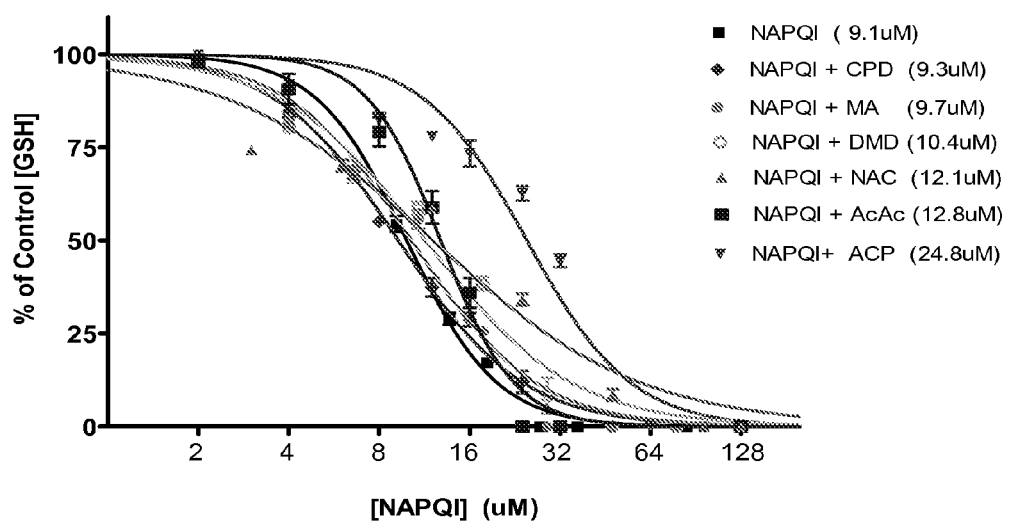
FIG. 3. Effects of 1,3-dicarbonyl enols (50 µM) on NAPQI (2-128 µM) induced GSH loss. Numbers in parentheses are respective $IC_{50}$ values.
Figure 4:
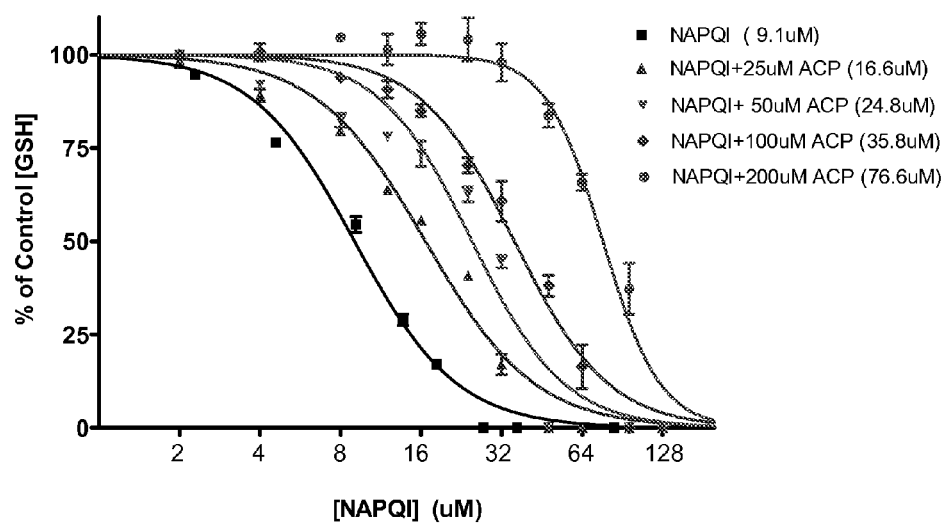
FIG. 4. Effects of 2-ACP (25-200 µM) on NAPQI (2-128 µM) induced GSH loss. Numbers in parentheses are respective $IC_{50}$ values.

The in chemico studies presented above demonstrate that 2-ACP can scavenge NAPQI and thereby prevent GSH sulfhydryl loss (FIGS. 3 and 4). This suggests that 2-ACP might be useful in preventing APAP hepatotoxicity in humans and laboratory animals. To test this premise, experimental groups (n=15-30/group) of fasted male C57 BL mice were administered equimolar i.p. doses of either 2-ACP or NAC (PEG400/PBS vehicle) at 20 minutes prior to acute oral (gavage) overdose of AAP (500 mg/kg)[14]. A separate group received the PEG400 vehicle 20 mins prior to AAP. Initial studies showed that neither NAC nor ACP alone caused significant changes in any hepatic parameter measured (see below). Vehicle control mice (n=10) received sequential injections of PEG400 (i.p. followed by oral). At several times post-AAP administration (2, 6, 24, 48 and 168 hrs), groups of mice were anesthetized in a carbon dioxide chamber and heparinized blood samples were collected. Samples were centrifuged and resulting serum was retained for analyses (see below). Livers were also excised, weighed and tissue samples were collected for histopathological evaluation. Remaining tissue was snap frozen in liquid nitrogen. Hepatotoxicity was determined by quantification of serum alanine aminotransferase (ALT) and aspartate aminotransferase (AST) using colorimetric assays. Serum lactate dehydrogenase (LDH) was also measured as an index of generalized AAP-induced organ toxicity. To evaluate the extent of cellular oxidative stress in liver homogenates, the unsaturated aldehyde by-products of lipid peroxidation, HNE and malondialdhyde (MDA), were determined according to a modification of the Gerard-Monnier et al. method[27]. In addition, soluble thiol contents were measured in homogenates according to LoPachin et al.[44].

Figure 5:
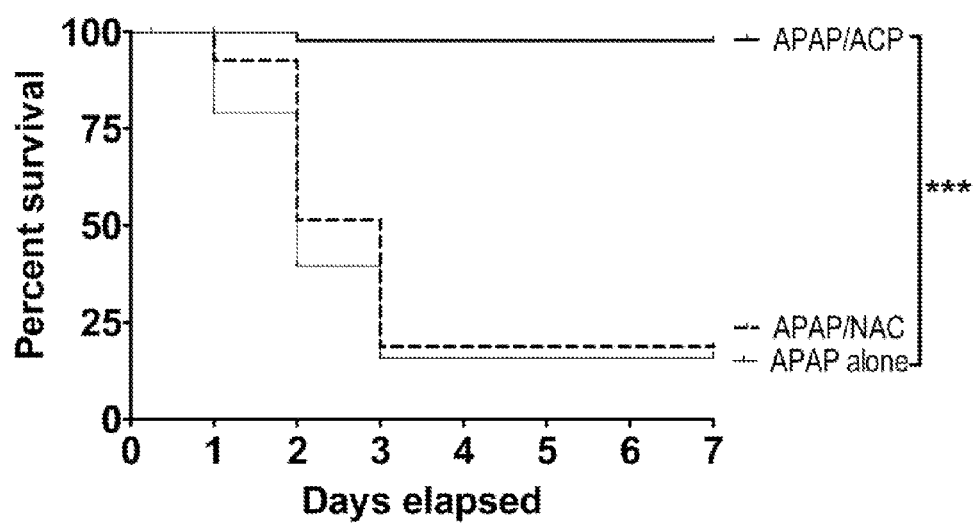
FIG. 5. Effects of i.p. 2-ACP (2.40 mmol/kg) or equimolar N-acetylcysteine (NAC) on oral acetaminophen (APAP) (500 mg/kg)-induced hepatotoxicity in mice (n=15-30/group). Kaplan-Meier survival curves illustrate the cumulative percent daily lethality in the APAP alone, APAP/NAC and APAP/ACP groups. Joining line indicates statistically significant differences in treatment groups at ***$p<0.001$ level of significance.
Figures 6A, 6B:
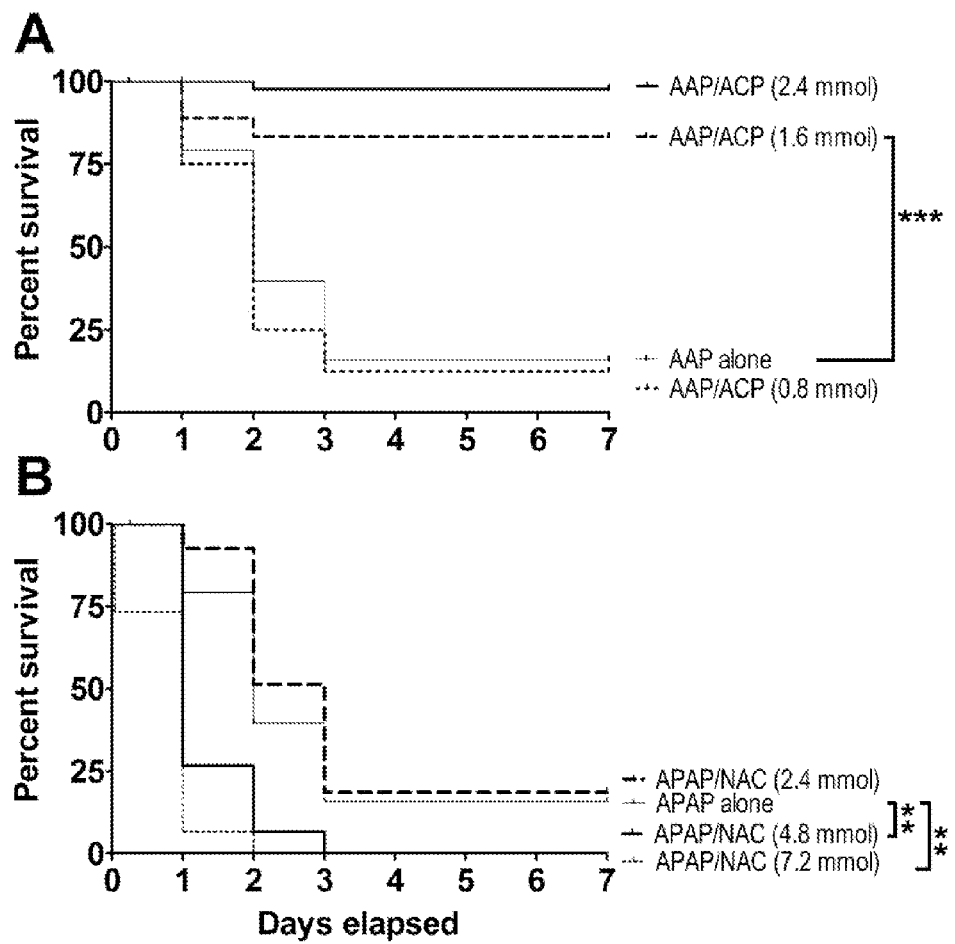
FIG. 6A-6B. (A). Dose-dependency of i.p. 2-ACP (0.80-2.40 mmol/kg) on oral acetaminophen (AAP or APAP) (500 mg/kg)-induced lethality. (B). Dose-dependency of i.p. NAC (2.40-7.20 mmol/kg) on oral APAP-induced lethality. Kaplan-Meier survival curves illustrate the cumulative percent daily lethality in the APAP alone, APAP/NAC and APAP/ACP groups (n=15 mice/group). Joining line indicates statistically significant differences in treatment groups at *$p<0.001$ and $p<0.01$ levels of significance.

The Kaplan-Meier survival data presented in FIG. 5 indicate that i.p. 2-ACP provided nearly complete protection from acute AAP-induced lethality, whereas i.p. NAC was ineffective. Specifically, oral APAP overdose administered to mice was nearly 90% lethal within 72 hrs (FIG. 5). However, 2-ACP (2.40 mmol/kg) given i.p. 20 minutes prior to intoxication completely prevented APAP lethality over a 7 day experimental period. 2-ACP hepatoprotection was dose-dependent, although it occurred over a narrow dose-range (FIG. 6A). In contrast, pretreatment with i.p. NAC over a broad dose-range (4.80-7.20 mmol/kg) was not protective and instead accelerated the rate of APAP lethality (FIG. 6B). Measurements of several biochemical indices of hepatocyte death (plasma ALT, AST and LDH) and oxidative stress (liver thiol loss and unsaturated aldehyde content) indicated that 2-ACP, but not NAC, prevented APAP-induced liver cell death (data not shown).

Figures 7A, 7B:
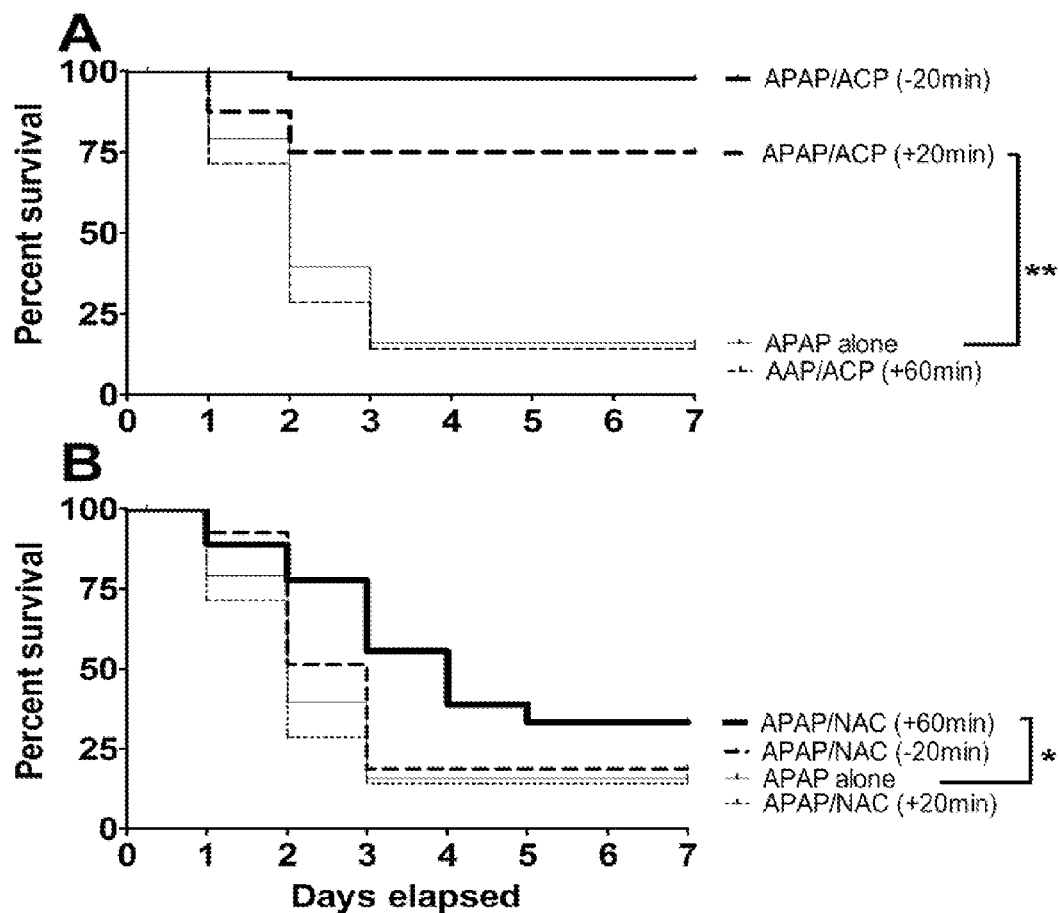
FIG. 7A-7B. Temporal-dependency of i.p. 2-ACP (A) (2.40 mmol/kg) or equimolar NAC (B) on oral APAP (500 mg/kg)-induced lethality. Hepatoprotectants were administered 20 mins before (−20), 20 mins after (+20) or 60 mins after (+60) APAP intoxication. Kaplan-Meier survival curves illustrate the cumulative percent daily lethality in the APAP alone, APAP/NAC and APAP/ACP groups (n=15 mice/group). Joining line indicates statistically significant differences in treatment groups at **$p<0.01$ and *$p<0.05$ levels of significance.

Histopathological analyses confirmed hepatocyte preservation and showed that i.p. pretreatment with 2-ACP prevented the liver centrilobular necrosis that characterizes APAP hepatotoxicity, whereas i.p. NAC did not stop this damage (data not shown). Studies designed to determine the temporal dependency of hepatoprotection showed that 2-ACP (2.40 mmol/kg, i.p.) afforded complete protection when administered 20 minutes before (−20) or after (+20) APAP intoxication, whereas the +60 time point was ineffective (FIG. 7A). NAC (2.40 mmol/kg, i.p.) was not protective at either 20 minute (±) time points, although when administered 60 minutes (+60) after APAP, NAC partially improved the survival of intoxicated mice (FIG. 7B)[14]. Although pharmacokinetic differences might be involved, the corresponding temporal nature of hepatoprotection could indicate that 2-ACP and NAC block different stages of APAP-induced hepatotoxicity (see below). Oral gavage administration of 2-ACP (2.40 mmol/kg) 20 minutes before oral APAP intoxication provided modest improvements in APAP survival rate (data not shown). This route-dependent decrease in effectiveness is related to the susceptibility of β-diketones to acid-catalyzed reactions (e.g., aldol condensation) that can occur in the stomach. In support of this, buffering the gavage solution (HEPES buffer, pH 9.0) or increasing the dose (4.80 mmol/kg) improved oral 2-ACP hepatoprotection (data not shown). In contrast to the i.p., oral NAC (2.40 mmol/kg) administration provided complete protection against APAP-induced lethality (data not shown).

Figure 8:
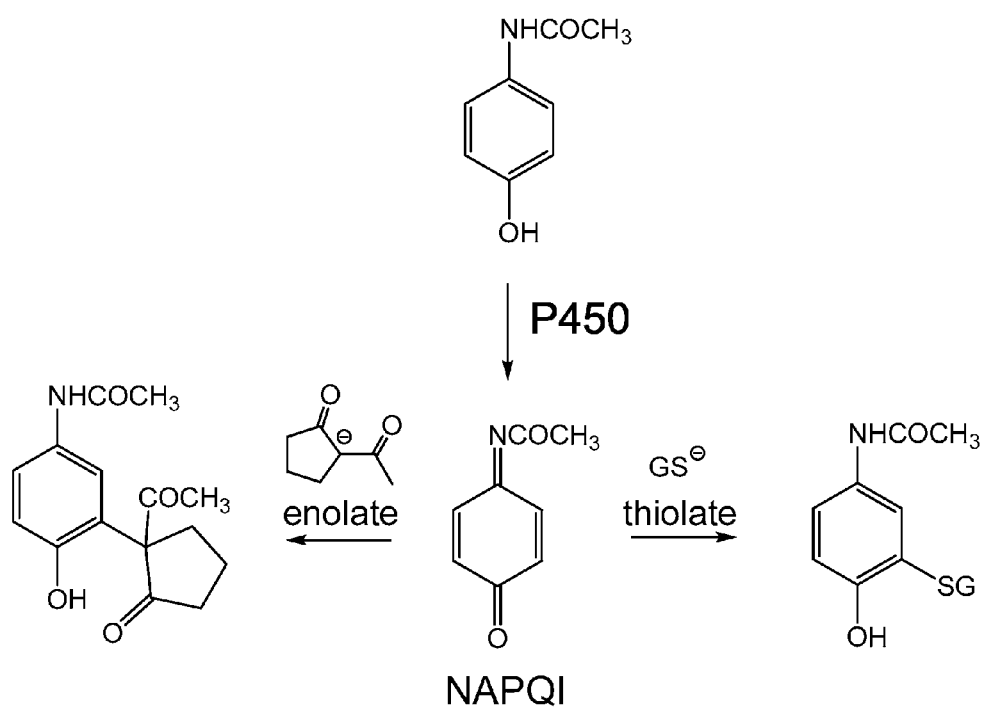
FIG. 8. Diagram showing cytochrome P450 metabolism of acetaminophen to the electrophilic metabolite, NAPQI, and the subsequent adduct-forming reactions with the enolate of 2-ACP or the GSH thiolate.

The present study has shown that 2-ACP can provide significant protection in a well-characterized animal model of APAP hepatotoxicity. 2-ACP does not simply delay the onset of AAP hepatotoxicity, but rather provides long-term protection as evidenced by animal survival (FIG. 5). HSAB calculations and corroborative in chemico studies indicate that the anionic enolate of 2-ACP is a soft nucleophile that can form 1,4-Michael adducts with soft electrophiles of different chemical classes; e.g., quinones and α,β-unsaturated aldehyde derivatives (see also LoPachin et al.[55]). With respect to hepatoprotection, 2-ACP may act as a surrogate nucleophilic target for NAPQI, which thereby completely arrests the subsequent oxidative stress cascade (FIG. 8). Relative to NAC, 2-ACP is a stronger acid ($pK_a$=7.8 vs. 9.6), which means that at physiological pH (7.4) the enolate nucleophile concentration of this β-diketone is significantly higher (~30%) than the thiolate concentration of NAC (<1%). Consequently, more of the 2-ACP nucleophile is available to scavenge electrophilic toxicants such as the oxidative metabolites of APAP (NAPQI, pBQ) and the type-2 alkene end-products of oxidative stress; e.g., acrolein, HNE. In addition, the flexible β-diketone structure of 2-ACP allows bidentate metal ion coordination and hence chelation[21,54]. Therefore, the cytoprotective mechanism of 2-ACP might also involve chelation, which would reduce the cellular free radical load by inhibiting the metal-catalyzed Fenton reaction.

As alluded to above, NAC is a relatively poor target for NAPQI because only a small proportion (<1%) of the cysteine sulfhydryl groups will be in the reactive anionic state. Indeed, previous research has suggested that NAC does not scavenge NAPQI and therefore cannot prevent the initial phase. Rather, NAC hepatoprotection probably involves an alternative mechanism that impacts the later developing toxic phase; e.g., free radical trapping, increased GSH synthesis or enhanced mitochondrial energy production[13,18,42,74,92]. The observation that i.p. NAC provided protection only at 60 minutes after APAP administration is consistent with such a delayed hepatoprotective mechanism (FIG. 7B).

Based on the relative protective abilities identified in the present studies and mechanistic understanding of 2-ACP and NAC, a critical attribute of 1,3-dicarbonyl hepatoprotection may be the ability to form Michael adducts with NAPQI and the soft electrophile mediators of oxidative stress. Because NAC is not a nucleophilic target for NAPQI at physiological pH, alternative indirect mechanisms such as biosynthetic conversion to GSH appear to be involved in the cytoprotection afforded by this thiol. Whereas the relative cytoprotective consequences of these additional NAC activities have not been determined, the present studies indicate that protection resulting from the direct chemical intervention of the 2-ACP enolate nucleophile might be a more efficacious process. Hence, 2-ACP or analogues or derivatives thereof would be useful in preventing the hepatotoxicity caused by TYLENOL® (acetaminophen) poisoning. Since the parent compound (APAP) is not an electrophile and therefore not a target for soft nucleophiles, it is possible that a 1,3-dicarbonyl could be added to the TYLENOL® formulation to prevent acute hepatotoxicity due to accidental or intentional overdose.

Disclosed Therapeutic Uses of Enolale Forming 1,3-Dicarbonyl Compounds

In addition to the obvious utility of 2-ACP (or an analogue or derivative) in acetaminophen toxicity, the ability to scavenge soft electrophiles from broad chemical classes; e.g., quinones (pBQ, NAPQI), unsaturated aldehydes (acrolein, 4-hydroxy-2-nonenal), metal ions (e.g., cisplatin, $Fe^2$), suggests that 2-ACP and analogous 1,3-dicarbonyl compounds have diverse pharmacotherapeutic implications. Thus, like acetaminophen, many clinically important drugs and chemicals are protoxicants that can be metabolized in the liver to reactive soft electrophiles; e.g., diclofenac, cyclophosphamide; valproic acid[23,84]. Although fewer in number, certain pharmacotherapeutic agents are themselves electrophiles (e.g., clopidogrel (PLAVIX®), esomeprazole (NEXIUM®)) and can participate in idiosyncratic drug-related toxicities[80]. The therapy-limiting toxicities mediated by parent compounds or corresponding reactive metabolites should be abated by 2-ACP administration. The ability to chelate metal ions suggests that the 1,3-dicarbonyl compounds could be useful in treating the painful sensory neuropathy that frequently develops during chemotherapy involving cisplatin and other platinum containing antineoplastic agents that is presumably mediated by the heavy metal component[86]. There is experimental evidence suggesting that 1,3-dicarbonyl (AcAc) chelation of the platinum ion could prevent neurotoxicity while preserving chemotherapeutic actions of cisplatin[64,72]. Cigarette smoking is essentially an efficient conduit for intake of metals, unsaturated carbonyls/aldehydes and other electrophilic chemicals that appear to be involved in mediating smoking related problems[25]. Thus, when taken simultaneously or on a prophylactic basis, 1,3-dicarbonyls might represent a method of pharmacotherapeutic intervention for minimizing the toxic consequences of these exposure conditions.

Based on the present finding that 2-ACP can prevent APAP hepatotoxicity, 1,3-dicarbonyl compounds should be useful in preventing or modifying other pathogenic states with a common molecular etiology of cellular oxidative stress. Thus, for example, 2-ACP might be a more effective pharmacotherapeutic approach than NAC in the management of chronic ethanol hepatotoxicity[10], radiocontrast nephrotoxicity[79] and radiation-induced cytotoxicity[58], all of which presumably involve oxidative cell damage. Similarly, 2-ACP is a rational, cytoprotective addendum to the organ preservation solutions currently used (e.g., University of Wisconsin (UW), Leeds and histidine-tryptophan-ketoglutarate (HTK) solutions), since the loss of organ transplant viability is a function of cellular oxidative stress injury[15,37,68]. Furthermore, it is becoming increasingly evident that cysteine/glutathione deficiency is a primary or secondary component of many disease states; e.g., viral infections—HIV/AIDS, influenza[8,17]; pulmonary diseases—cystic fibrosis, chronic obstructive pulmonary disease (COPD)[40,87]; and emotional disorders—obsessive-compulsive syndrome, trichotillomania—hair consumption[28]. In many cases, these conditions have been clinically improved through administration of NAC. The benefit is presumed to be related to increased enzymatic synthesis of GSH and subsequent suppression of oxidative stress (reviewed in[4,61]). However, as a relatively strong nucleophile with greater acidity (lower $pK_a$ value), 2-ACP could replace or supplement NAC as a therapeutic avenue in cysteine/glutathione deficiencies.

In summary, research detailed in this patent application demonstrates that 2-ACP can prevent hepatotoxicity-based lethality in an animal model of APAP poisoning. The present findings indicate a level of protection which is superior to that provided by NAC (MUCOMYST®), the current treatment of choice. The primary mechanism of cytoprotection involves enolate scavenging of the highly reactive electrophilic APAP metabolite, NAPQI, which completely truncates the ensuing oxidative stress cascade that otherwise causes liver cell death. The enolate cytoprotective mechanism is unlike that of conventional antioxidants such as tocopherols and carotenoids that presumably trap free radicals. In fact, the enolate nucleophiles can scavenge a variety of electrophilic toxicants from different chemical classes;

e.g., quinones, α,β-unsaturated carbonyl/aldehyde derivatives and metal ions. This spectrum of electrophile scavenging implicates broad therapeutic applications; e.g., treatment or prevention of acetaminophen poisoning, idiosyncratic drug toxicities, cisplatin neurotoxicity or the enhancement of preservation solutions. In contrast to the phytopolyphenols (phloretin, curcumin, resveratrol), which also are considered to have extensive clinical applications, the 1,3-dicarbonyls are water-soluble, bioavailable, chemically stable and non-toxic. The most efficacious of these compounds, 2-ACP and possibly, some newly designed analogues, are outstanding candidates for pharmacotherapeutic approaches to diseases and tissue injury conditions that have cellular oxidative stress as a molecular etiology.

Enolate Protection in Acute Ischemia-Reperfusion Injury of Rat Liver

Background.

Significant tissue damage occurs when blood flow to an organ (e.g., liver, heart or brain) is impaired (ischemia) and then subsequently restored (reperfusion). The resulting cell injury occurs as a consequence of the oxidative stress and mitochondrial dysfunction initiated during ischemia, with subsequent exacerbation of damage as a result of mitochondrial reoxygenation during reperfusion[96]. The ischemia-reperfusion (IR) sequence can occur either purposefully (e.g., during tissue resection and transplantation) or as part of a disease process (e.g., stroke, coronary artery occlusion). IR injury following cold preservation is a significant impediment to successful organ transplantation. Indeed, 15%-25% of donor livers do not recover full function and as many as 6% fail postoperatively[68]. Organ preservation for eventual transplantation is based on in situ perfusion with cold preservation solutions (e.g., University of Wisconsin Solution) and subsequent refrigerated storage in these solutions[97]. The preservation solutions mimic intracellular osmolarity and corresponding electrolyte composition and concentration and can maintain organs in a viable state for up to 48 hrs.

Prevention of I/R Injury Using 1,3-Dicarbonyl Compounds.

Figure 9:
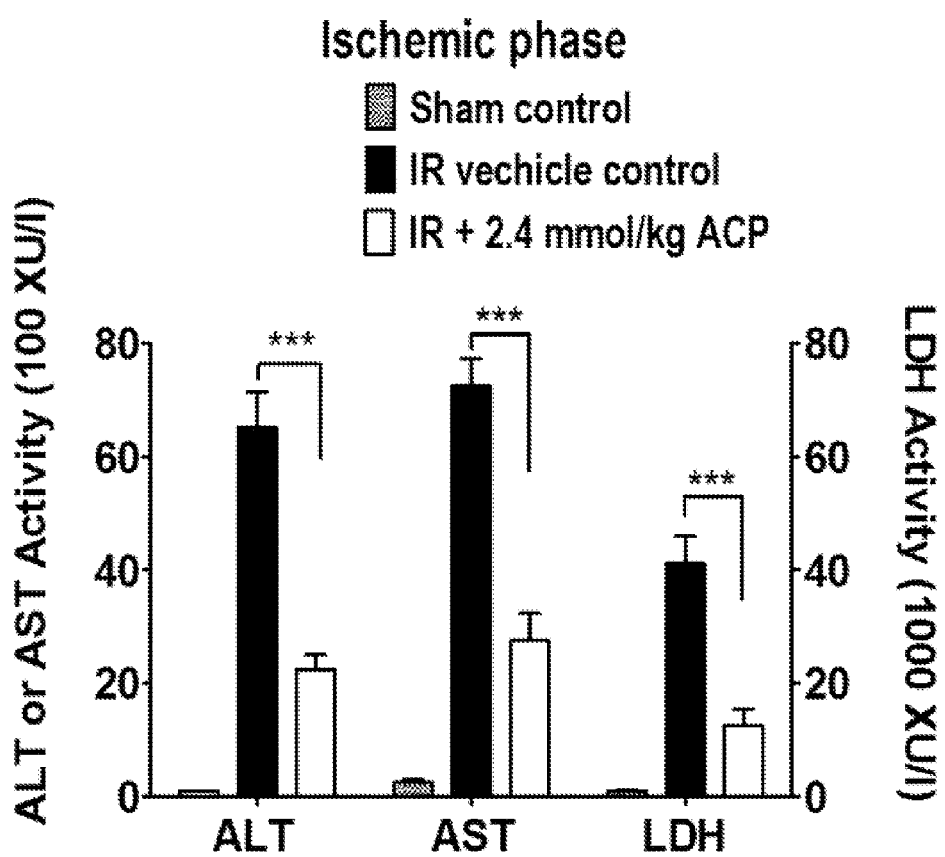
FIG. 9. Effect of 2-ACP on liver ischemia. 2-ACP (2.40 mmol/kg) or vehicle was injected i.p. 10 mins before clamping the portal vasculature for 45 mins. At the completion of the Ischemic phase, clamps were removed and the liver was reperfused for 180 mins. Following reperfusion, blood samples were removed for analysis of liver enzymes (ALT, AST) and LDH in plasma. Joining lines indicate statistically significant differences in treatment groups at ***P<0.001 level of significance.
Figure 10:
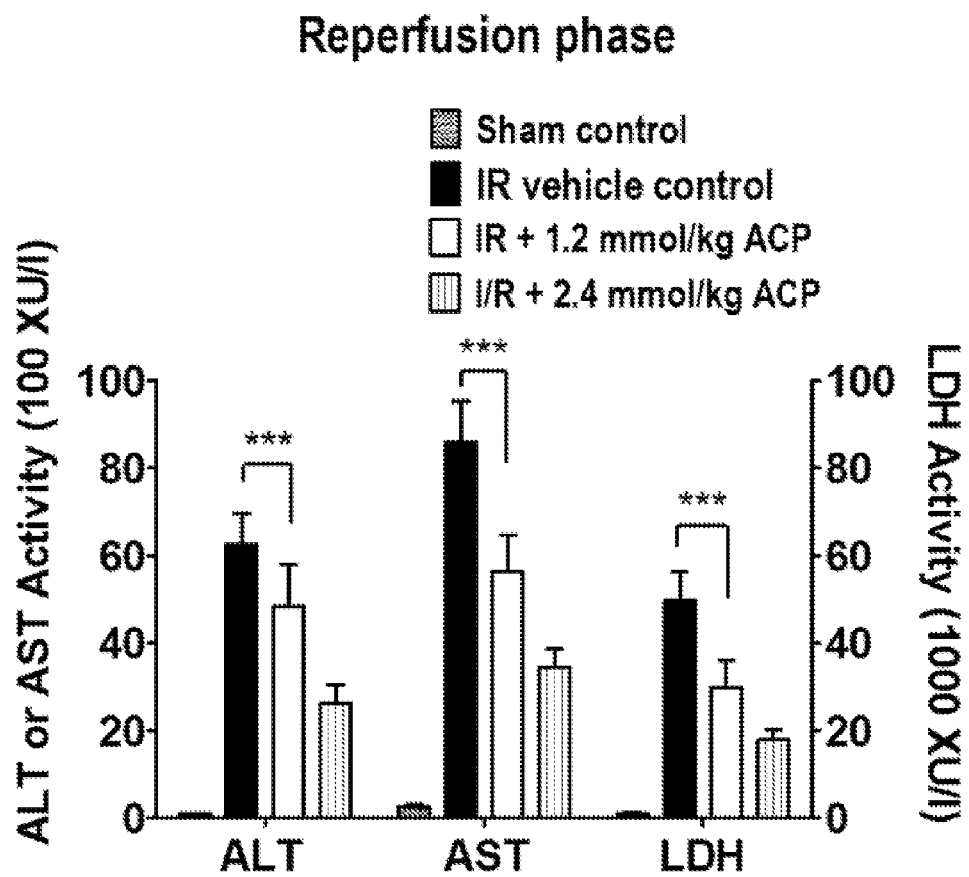
FIG. 10. Effect of 2-ACP on liver reperfusion. 2-ACP (2.40 mmol/kg) or vehicle was injected i.p. 10 mins before restoration of hepatic circulation (reperfusion phase). At the completion of reperfusion, blood samples were removed for analysis of liver enzymes (ALT, AST) and LDH (a general enzyme indicator of tissue injury) in plasma. Joining lines indicate statistically significant differences in treatment groups at ***P<0.001 level of significance.
Figure 11:
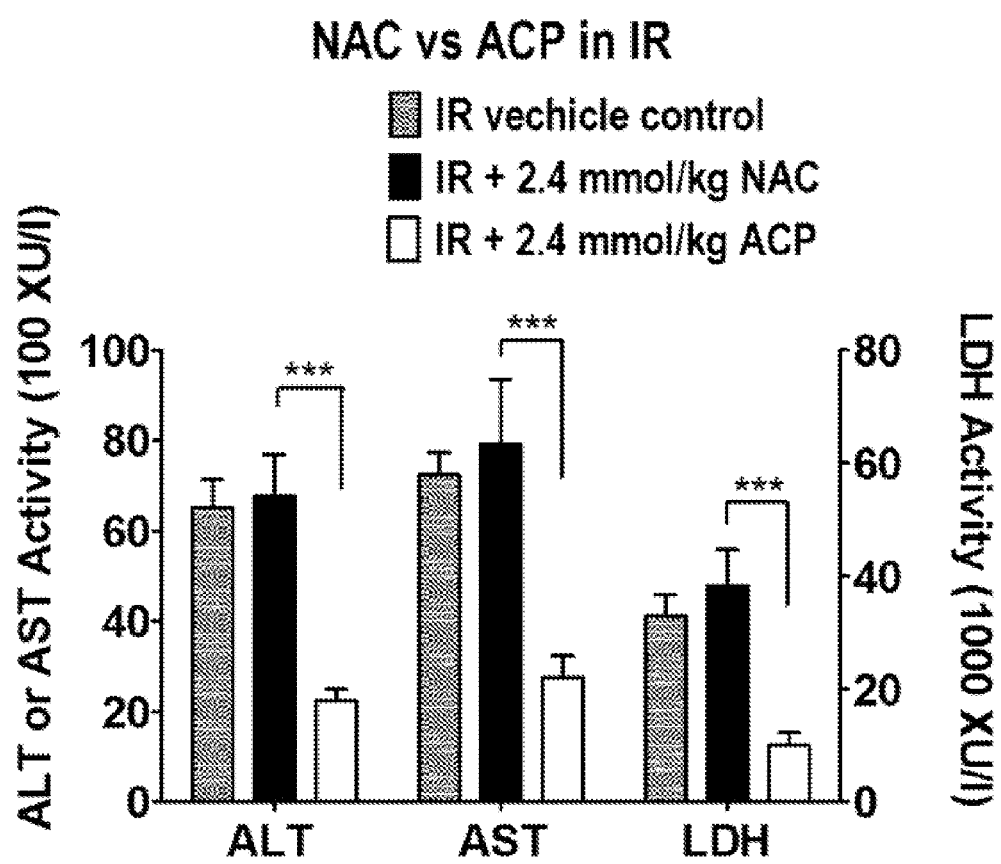
FIG. 11. Effect of 2-ACP versus NAC on liver reperfusion. 2-ACP (2.40 mmol/kg) or equimolar NAC was injected i.p. 10 mins before restoration of hepatic circulation (reperfusion phase). At the completion of reperfusion, blood samples were removed for analysis of liver enzymes (ALT, AST) and LDH (a general enzyme indicator of tissue injury) in plasma. Joining lines indicate statistically significant differences in treatment groups at ***P<0.001 level of significance.

IR injury is the pathophysiological basis for stroke, myocardial infarction and other organ failure. It is also an underlying cause of allograft rejection following tissue transplantation. To investigate the possibility that 2-ACP and other nucleophilic dicarbonyl derivatives might be useful in preventing IR-mediated organ damage, rats were anesthetized and I/R was induced by clamping the portal vein and hepatic artery using commercially available microclips placed at the porta hepatis. The ischemic state was maintained for 45 mins, which affected approximately 70% of the liver mass. Following removal of the microclamps, hepatic reperfusion was maintained for 180 min. Animals were then sacrificed and plasma samples were taken for subsequent analysis of lactate dehydrogenase (LDH; a general enzyme indicator of cell injury) and liver enzymes (AST and ALT). Experimental I/R groups (n=15/group) received i.p. administration of 1% DMSO in PBS (vehicle) or equimolar doses of test compound (2-ACP or NAC) 10 mins prior to either the ischemic or reperfusion phase. A sham group (laparotomy only) provided baseline data for the appearance of liver enzyme in plasma. As illustrated in FIG. 9, I/R-induced liver damage was associated with significant increases (compared to sham data) in the plasma activities of liver enzymes (ALT, AST) and LDH. This level of hepatocyte leakage indicates substantial irreversible cell injury. However, i.p. administration of 2-ACP prior to ischemia was associated with considerable reductions in the plasma appearance of liver enzymes caused by I/R (FIG. 9). This suggests hepatocyte protection during both ischemia and the subsequent reperfusion phase. Thus, prior 2-ACP administration is able to diminish the pathophysiological disposition of the ischemic phase. Further, amelioration of the ischemic phase truncates subsequent culmination of hepatocyte injury during reperfusion. To determine whether hepatoprotection was phase-specific and dose-dependent, 2-ACP (1.20-2.40 mmol/kg) was injected i.p. 10 mins prior to the restoration of hepatic circulation (reperfusion phase). Results show (FIG. 10) that this 2-ACP administration scenario provided substantial hepatocyte dose-dependent protection. This indicates that although the ischemia phase proceeded unabated, hepatoprotection was still possible when 2-ACP was administered prior to reperfusion. This emphasizes the pathophysiological relevance of reperfusion and suggests that 2-ACP can reduce the oxidative stress that characterizes this phase[96]. In contrast, i.p. administration of equimolar NAC prior to ischemia (not shown) or reperfusion (FIG. 11) did not prevent I/R liver injury.

As indicated cellular oxidative stress is a major component of IR induced organ damage and therefore the observed hepatoprotection was likely related to the ability of 2-ACP to chelate metal ions and thereby inhibit free radical generation via the metal-catalyzed Fenton reaction. In addition, 1,3-dicarbonyls can scavenge unsaturated aldehydes (e.g., acrolein, HNE) that directly mediate cell injury during oxidative damage.

Conclusions: Use of 1,3-Dicarbonyl Derivatives in IR Injury and Organ Preservation Solutions:

The present research has shown that 2-ACP is hepatoprotective in an experimental model of IR injury. Although reactive oxygen species (ROS) are clearly involved in IR oxidative stress, antioxidant drugs that target ROS have performed poorly in pre-clinical trials and are not currently in clinical use. This lack of success reflects a failure to understand the very fast kinetics of ROS generation and to recognize the complexity of corresponding mechanisms and cellular sources[95]. The 1,3-dicarbonyls are not antioxidants (i.e., they do not scavenge ROS), instead these compounds are carbon-based enolate nucleophiles that have multiple sites of action within the oxidative stress cascade; i.e., they inhibit the ROS generating Fenton reaction and they scavenge highly toxic unsaturated aldehyde electrophiles that are the penultimate mediators of oxidative damage[54,91]. Based on this reasoning, 1,3-dicarbonyl derivatives are expected to be useful in preventing tissue injury associated with stroke and other events involving transient tissue oxygen deprivation. Similarly, IR-induced oxidative stress is the underlying cause of allograft failure following transplantation. The preservation solutions used for donor organ resection and storage (e.g., UW, HTK and Leeds solutions) uniformly contain antioxidants (e.g., allopurinol, carvedilol). Nonetheless, it is recognized that cell damage is still an issue and, consequently, there is substantial room for improvement of these solutions[15,68,94]. Based on the multimodal mechanism of cytoprotection against oxidative stress, the addition of a 1,3-dicarbonyl derivative could augment the cytopreservative capabilities of these solutions.

REFERENCES

1. Albano, E., Rundgren, M., Harvison, P. J., Nelson, S. D. and Moldeus, P. (1985). Mechanisms of N-acetyl-p-benzoquinone imine cytotoxicity. *Mole. Pharmacol.* 28, 306-11.

2. Aggarwal, B. B., Sundaram, C., Malani, N. and Ichikawa, H. (2007) Curcumin: the Indian solid gold. *Adv. Exp. Med. Biol.* 595, 1-75.
3. Ak, T. and Gulcin, 1. (2008) Antioxidant and radical scavenging properties of curcumin. *Chem.-Biol. Inter.* 174, 27-37.
4. Atkuri, K. R., Mantovani, J. J., Herzenberg, L. A. and Herzenberg, L. A. (2007). N-Acetylcysteine—a safe antidote for cysteine/glutathione deficiency. *Curr Op Pharmacol.* 7, 355-359.
5. Ballantyne B, Cawley T J (2001). 2,4-Pentanedione: toxicology update. *J. Appl. Toxicol.* 21, 165-171.
6. Begum, A. N., Jones, M. R., Lim, G. P., Morihara, T., Kim, P., Heath, D. D., Rock, C. L., Pruitt, M. A., Yang, R., Hudspeth, B., Hu, S., Faull, K. F., Teter, B., Cole, G. M. and Frautschy, S. A. (2008) Curcumin structure-function, bioavailability and efficacy in models of neuroinflammation and Alzheimer's disease. *J. Pharmacol. Exp. Ther.* 326, 196-208.
7. Bravo, L. (1998) Polyphenols: chemistry, dietary sources, metabolism and nutritional significance. *Nutr. Rev.* 56, 317-333.
8. Breitkreutz, R., Pittack, N., Nebe, C. T., Schuster, D., Brust, J., Beichert, M., Hack, V., Volker, D. (2000). Improvement of immune functions in HIV infection by sulfur supplementation: Two randomized trials. *J. Mole. Med.* 78, 55-62.
9. Bug, T. and Mayr, H. (2003) Nucleophilic reactivities of carbanions in water: the unique behavior of the malodinitrile anion. *J. Am. Chem. Soc.* 125, 12980-12986.
10. Cederbaum, A. I., Lu, Y. and Wu, D. (2009). Role of oxidative stress in alcohol-induced liver injury. *Arch. Toxicol.* 83, 519-548.
11. Chattaraj, P. K., Sarkar, U. and Roy, D. R. (2006). Electrophilicity index. *Chem. Rev.* 106, 2065-2091.
12. Coles, B. (1984-85) Effects of modifying structure on electrophilic reactions with biological nucleophiles. *Drug Met. Rev.* 15, 1307-1334.
13. Corcoran, G. B., Todd, E. L., Racz, W. J., Hughs, C. V., Smith, C. V. and Mitchell, J. R. (1985). Effects of N-acetylcysteine on the disposition and metabolism of acetaminophen in mice. *J. Pharmacol Exp. Ther.* 232, 857-863.
14. Corcoran, G. B., Racz, W. J., Smith, C. V. and Mitchell, J. R. (1985). Effects of N-acetylcysteine on acetaminophen covalent binding and hepatic necrosis in mice. *J. Pharmacol Exp. Ther.* 232, 864-872.
15. Corps, C. L., Shires, M., Crellin, D., Smolenski, R., Potts, D., Pratt, J. and Lodge, J. P. A. (2009). Influence on energy kinetics and histology of different preservation solutions seen during cold ischemia in the liver. *Transp. Proc.* 41, 4088-4093.
16. Dahlin, D. C. and Nelson, S. D. (1982). Synthesis, decomposition kinetics and preliminary toxicological studies of pure N-acetyl-p-benzoquinone imine, a proposed toxic metabolite of acetaminophen. *J. Med. Chem.* 25, 885-886.
17. DeFlora, S., Grassi, C. and Carati, L. (1997). Attenuation of influenza-like symptomatology and improvement of cell-mediated immunity with long-term N-acetylcysteine treatment. *Eur. Resp. J.* 10, 1535-1541.
18. De Flora S, Issotti A, D'Agostini F and Balansky M (2001) Mechanisms of N-acetylcysteine in the prevention of DNA damage and cancer, with special reference to smoking-related end-points. *Carcinogenesis* 22: 999-1013.
19. Dietze, E. C., Schafer, A., Omichinski, J. G. and Nelson, S. D. (1997). Inactivation of glyceraldehdye-3-phosphate dehydrogenase by a reactive metabolite of acetaminophen and mass spectral characterization of an arylated active site peptide. *Chem. Res. Toxicol.* 10, 1097-1103.
20. Dodd, D. E., Garman, H. and Pritts, I. M. (1986). 2,4-Pentanedione: 9-day and 14-week vapor inhalation studies in Fischer-344 rats. *Fund. Appl. Toxicol.* 7, 329-336.
21. Eames J (2009) Acid-base properties of enols and enolates. In *The Chemistry of Metal Enolates* (Zablicky J ed) Chapt 8, pp 411-460. John Wiley & Sons, West Sussex, England.
22. Elms, A. R., Owen, K. P., Albertson, T. and Sutter, M. E. (2011). Fatal myocardial infarction associated with intravenous N-aceytlcysteine error. 4, 54-58.
23. Erve, J. C. L. (2006). Chemical toxicology: reactive intermediates and their role in pharmacology and toxicology. *Expert Opin Drug Metab Toxicology* 2, 923-946.
24. Esterbauer, H., Schaur, R. J. and Zollner, J. (1991). Chemistry and biochemistry of 4-hydroxynonenal, malonaldehyde and related aldehydes. *Free Rad. Biol. Med.* 11: 81-128.
25. Fujioka, K. and Shibamoto, T. (2006). Determination of toxic carbonyl compounds in cigarette smoke. *Environ Toxicol.* 21, 47-54.
26. Galati, G. and O'Brien, P. J. (2004) Potential toxicity of flavonoids and other dietary phenolics: significance for their chemopreventive and anticancer properties. *Free Rad. Biol. Med.* 37, 287-303.
27. Gerard-Monnier, D., Erdelmeier, I., Regnard, K., Moze-Henry, N., Yadan, J. C. and Chaudiere, J. (1998). Reactions of I-methyl-2-phenylindole with malondialdehyde and 4-hydroxyalkenals. Analytical applications to a colorimetric assay of lipid peroxidation. *Chem. Res. Toxicol.* 11, 1176-83.
28. Grant, J. E., Odlaug, B. L., Kim, W. S. (2009). N-Acetylcysteine, a glutamate modulator, in the treatment of trichotillomania: a double-blind, placebo-controlled study. *Arch Gen. Psych.* 66, 756-763.
29. Halliwell, B. (2006). Oxidative stress and neurodegeneration: where are we now? *J. Neurochem.* 97, 1634-1658.
30. Hinson, J. A. (1992) Role of covalent and noncovalent interactions in cell toxicity: effects on proteins. *Ann. Rev. Pharmacol. Toxicol.* 32, 471-510.
31. Hinson, J. A., Roberts, D. W and James, L. P. (2010). Mechanisms of acetaminophen-induced liver necrosis. *Handb. Exp. Pharmacol.* 196, 369-405.
32. Heard, K. J. (2008). Acetylcysteine for acetaminophen poisoning. *N. Engl. J. Med.* 359, 285-292.
33. Jaeschke, H., Gores, G. J., Cederbaum, A. I., Hinson, J. A., Pessayre, D. and Lemasters, J. J. (2002). Mechanisms of hepatotoxicity. *Toxicol. Sci.* 65, 166-176.
34. Jaeschke, H., Knight, T. R., Bajt, M. L. (2003). The role of oxidant stress and reactive nitrogen species in acetaminophen hepatoxicity. *Toxicol. Letters* 144, 279-288.
35. James, L. P., Mayeux, P. R. and Hinson, J. A. (2003). Acetaminophen-induced hepatotoxicity. *Drug Met. Disp.* 31, 1499-1506.
36. Jaramillo, P., Periz, P., Contreas, R., Tiznada, W. and Fuentealba, P. (2006) Definition of a nucleophilicity scale. *J Phys. Chem.* 110, 8181-8187.
37. Jegatheeswaran, S. and Siriwardena, A. K. (2010). Experimental and clinical evidence for madificatgion of hepatic ischaemia-reperfusion injury by N-aceylcysteine during major liver surgery. *Hepato. Panc. Bil.* 13, 71-78.

38. Jenner, P. (2003). Oxidative stress in Parkinson's disease. *Ann. Neurol.* 53, S26-38.
39. Jollow, D. J., Mitchell, J. R., Potter, W. Z., Davis, D. C., Gillette, J. R. and Brodie, B. B. (1973). Acetaminophen-induced hepatic necrosis. II. Role of covalent binding in vivo. *J. Pharmacol. Exp. Ther.* 187, 195-202.
40. Kasielski, M. and Nowak, D. (2001). Long-term administration of N-acetylcysteine decreases hydrogen peroxide exhalation in subjects with chronic obstructive pulmonary disease. *Resp. Med.* 95, 448-456.
41. Kehrer, J. P. and Biswal, S. S. (2000) The molecular effects of acrolein. *Toxicol Sci.* 57, 6-15.
42. Lauterburg B H, Corcoran G B and Mitchell J R (1983) Mechan of action of N-acetylcysteine in the protection against the hepatotoxicity of acetaminophen in rats in vivo. *J Clin Invest* 71: 980-991.
43. Lin, M. T. and Beal, M. F. (2006) Mitochondrial dysfunction and oxidative stress in neurodegenerative diseases. *Nature* 443, 787-795.
44. LoPachin, R. M., Schwarcz, A. I., Mansukhani, S., Das, S. (2004) In Vivo and In Vitro Effects of Acrylamide on Synaptosomal Neurotransmitter Uptake and Release. *NeuroToxicology.* 25: 349-363.
45. LoPachin, R. M. and DeCaprio, A. P. (2005) Protein adduct formation as a molecular mechanism of neurotoxicity. *Toxicol. Sci.* 86, 214-225.
46. LoPachin, R. M. and Barber, D. S. (2006). Synaptic cysteine sulfhydryl groups as targets of electrophilic neurotoxicants. *Tox. Sci.* 94, 240-255.
47. LoPachin, R. M., Barber, D. S., Geohagen, B. C., Gavin, T., He, D. and Das, S. (2007). Structure-toxicity analysis of Type-2 alkenes: in vitro neurotoxicity. *Tox. Sci.* 95: 136-146.
48. LoPachin, R. M., Gavin, T., Geohagen, B. C. and Das, S. (2007). Neurotoxic mechanisms of electrophilic type-2 alkenes: soft-soft interactions described by quantum mechanical parameters. *Tox. Sci.* 98: 561-570.
49. LoPachin, R. M., Barber, D. S. and Gavin, T. (2008). Molecular mechanisms of the conjugated α,β-unsaturated carbonyl derivatives: relevance to neurotoxicity and neurodegenerative diseases. *Tox. Sci.* 104, 235-249.
50. LoPachin, R. M., Gavin, T. and Barber, D. S. (2008). Type-2 alkenes mediate synaptotoxicity in neurodegenerative diseases. *NeuroToxicology* 29, 871-882.
51. LoPachin, R. M. and Gavin, T. (2008). Acrylamide-induced nerve terminal damage: relevance to neurotoxic and neurodegenerative mechanisms. *J. Agric. Food Chem.* 56, 5994-6003.
52. LoPachin, R. M., Gavin, T., Geohagen, B. C. and Das, S. (2009). Synaptosomal toxicity and nucleophilic targets of 4-hydroxy-2-nonenal. *Tox. Sci.* 107: 171-181.
53. LoPachin, R. M., Gavin, T., Petersen, D. R. and Barber, D. S. (2009). Molecular mechanisms of 4-hydroxy-2-nonenal and acrolein toxicity: nucleophilic targets and adduct formation. *Chem. Res. Toxicol.* 22: 1499-1508.
54. LoPachin, R. M., Gavin, T., Geohagen, B. C., Zhang, L., Casper, D., Lekrhaj, R. and Barber, D. S. (2011). β-Dicarbonyl Enols: A New Class of Neuroprotectants. *J. Neurochem* 116: 132-143.
55. LoPachin, R. M., Gavin, T., DeCaprio, A. P. and Barber, D. S. (2012). Application of the hard and soft, acids and bases (HSAB) theory to toxicant-target interactions. *Chem. Res. Toxicol.* 25: 239-251.
56. LoPachin, R. M. and Gavin, T. (2012) Molecular mechanism of acrylamide neurotoxicity: lessons learned from organic chemistry. *Environ Health Persp* 120, 1650-7.
57. Loudon, G. M. (2002) *Organic Chemistry* (4$^{th}$ ed.) Oxford University Press, NY; Chapt. 22; pg. 997.
58. Mansour, H. H., Hafez, H F, Fahmy, N. M. and Hanafi, N. (2008). Protective effect of N-acetylcysteine against radiation induced DNA damage and hepatic toxicity in rats. *Biochem. Pharmacol.* 75, 773-780.
59. Madsen, K. G., Olsen, J., Skonberg, C., Hansen, S. H. and Jurva, U. (2007). Development and evaluation of an electrochemical method for studying reactive phase-I metabolites: correlation to in vitro drug metabolism. *Chem. Res. Toxicol.* 20, 821-831.
60. Martyniuk, C. J., Fang, B., Koomen, J. M., Gavin, T., LoPachin, R. M., and Barber, D. S. Molecular Mechanism of Glyceraldehyde-3-Phosphate Dehydrogenase Inactivation by α,β-Unsaturated Carbonyl Derivatives. *Chem. Res. Toxicol.* 24: 2302-2311.
61. Millea, P. J. (2009). N-Acetylcysteine; Multiple clinical applications. *Am Fam. Phy.* 80, 265-269.
62. Miner, D. J. and Kissinger, P. T. (1979). Evidence for the involvement of N-acetyl-p-quinoneimne in acetaminoaphen metabolism. *Biochem. Pharmacol.* 28, 3285-3290.
63. Mitchell, J. R., Jollow, D J., Potter, W. Z., Davis, D. C., Gillette, J. R. and Brodie, B. B. (1973). Acetaminophen-induced hepatic necrosis. I. Role of drug metabolism. *J. Pharmacol. Exp. Ther.* 187, 211-217.
64. Mitchell, J. R., Jollow, D J., Potter, W. Z., Gillette, J. R. and Brodie, B. B. (1973). Acetaminophen-induced hepatic necrosis. I V. Protective role of glutathione. *J. Pharmacol. Exp. Ther.* 187, 185-194.
65. Muscella A, Calabriso N, Vetrugno C, Urso L, Fanizzi F P, De Pascali S A, Marsigliante S. (2010) Sublethal concentrations of the platinum (II) complex [Pt(O,O'-acac) (γ-acac) (DMS)] alter the motility and induce anoikis in MCF-7 cells. *Brit J Pharmacol* 160: 1362-1377.
66. Nelson, S. D. and Pearson, P. G. (1990) Covalent and noncovalent interactions in acute lethal cell injury caused by chemicals. *Ann. Rev. Pharmacol. Toxicol.* 30, 169-195.
67. Ostapowicz, G., Fontana, R J., Schiodt, F. V. et al. (2002). Results of a prospective study of acute liver failure at 17 tertiary care centers in the U.S. *Ann. Intern. Med.* 137, 947-954.
68. Park, S. W. and Lee, S. M. (2008). Antioxidant and prooxidant properties of ascorbic acid on hepatic dysfunction induced by cold ischemia/reperfusion. *Eur. J. Pharmacol.* 580, 401-406.
69. Petersen, D. R., and Doorn, J. A. (2004). Reactions of 4-hydroxynonenal with proteins and cellular targets. *Free Rad. Biol. Med.* 37, 937-945.
70. Qiu, Y., Benet, L. Z. and Burlingame, A. L. (1998). Identification of the hepatic protein targets of reactive metabolites of acetaminophen in vivo in mice using two-dimensional gel electrophoresis and mass spectrometry. *J. Biol. Chem.* 273, 17940-17953.
71. Rosen, G. M., Rauckman, E J., Ellington, S. P., Dahlin, D. C., Christie, J. L. and Nelson, S. D. (1983). Reduction and glutathione conjugation reactions of N-acetyl-p-benzoquinone imine and two dimethylated analogues. *Mole. Pharmacol.* 25, 151-157.
72. Rybak L P, Ravi R, Somani S M. (1995) Mechanism of protection by diethyldithiocarbomate against cisplatin ototoxicity: antioxidant system. *Fund Appl Toxicol.* 26: 293-300.
73. Saito C, Zwingmann C and Jaeschke H (2010) Novel mechanisms of protection against acetaminophen hepatotoxicity in mice by glutathione and N-acetylcysteine. *Hepatology* 51: 246-254.

74. Satoh, T. and Lipton, S. A. (2006) Redox regulation of neuronal survival mediated by electrophilic compounds. *Trends Neurosci.* 30, 37-45.
75. Sandilands, E. A. and Bateman, D. N. (2009). Adverse reactions associated with acetylcysteine. *Clin. Tox.* 47, 81-88.
76. Sayre, L. M., Perry, G. and Smith, M. A. (2008) Oxidative stress and neurotoxicity. *Chem. Res. Toxicol.* 21, 173-188.
77. Schultz, T. W., Netzeva, T. I., Roberts, D. W. and Cronin, M. T. D. (2005) Structure-toxicity relationships for the effects to *Tetrahymena pyriformis* of aliphateic carbonyl-containing α,β-unsaturated chemicals. *Chem. Res. Toxicol.* 18, 330-341.
78. Schultz, T. W., Carlson, R. E., Cronin, M. T. D., Hermens, J. L. M., Johnson, R., O'Brien, P. J., Roberts, D. W., Siraki, A., Wallace, K. B. and Veith, G. D. (2006). A conceptual framework for predicting the toxicity of reactive chemicals: modeling soft electrophilicity. *SAR QSAR Eviron. Res.* 17, 413-428.
79. Shalansky, S. J., Pate, G. E., Levin, A. and Webb, J. G. (2005) N-acetylcysteine for prevention of readiocontrast induced nephrotoxicity: the importance of dose and route of administration. *Heart* 91: 997-999.
80. Singh, J., Petter, R. C., Baillie, T. A. and Whitty, A. (2011) The resurgence of covalent drugs. *Nat Rev/Drug Disc.* 10, 307-317.
81. Smilkstein, M. J., Knapp, G. I., Kulig, K. W. and Rumack, B. H. (1988). Efficacy of oral N-acetylcysteine in the treatment of acetaminophen overdose. *N. Engl. J. Med.* 319, 1557-1562.
82. Smith, M. B. and March, J. (2001) *Advanced Organic Chemistry* (5$^{th}$ ed.) John Wiley and Sons, NY; Chapt. 15; pg. 1022.
83. Spencer, P. S. (2000). 2,4-Pentanedione. *Experimental and Clinical Neurotoxicology* (2$^{nd}$ ed.) Oxford University Press, NY; Part Two, pg 966.
84. Stachulski, A. V., Baillie, T. A., Park B. K., Obach, R. S., Dalvie, D. K. et al. (2012) The generation, detection and effects of reactive drug metabolites. *Med. Res. Rev.* 0, 1-96.
85. Schwobel, J. A. H., Koleva, Y. K., Enoch, S. J., Bajot, F., Hewitt, M., Madden, J. C., Roberts, D. W., Schultz, T. W. and Cronin, M. T. D. (2011). Measurement and estimation of electrophilic reactivity for predictive toxicology. *Chem. Rev.* 111, 2562-2596.
86. Thompson S W, Davis L E, Kornfeld M, Hilgers R D, Standefers J C. (1984). Cisplatin neuropathy: clinical, electrophysiologic, morphologic and toxicologic studies. *Cancer* 54, 1269-1275.
87. Tirouvanziam, R., Conrad, C. K., Bottiglieri, T., Herzenberg, L. A., Moss, R. B. and Herzenberg, L. A. (2006). High dose oral N-acetylcysteine, a glutathione prodrug, modulates inflammation in cystic fibrosis. *Proc. Natl. Acad Sci.* 103, 4628-4633.
88. Wang, Y., Pan, M., Cheng, A., Lin, L., Ho, Y., Hsieh, C. and Lin, J. (1997) Stability of curcumin in buffer solutions and characterization of its degradation products. *J. Pharmaceut. Biomed. Analy.* 15, 18667-1876.
89. Weber, W. M., Hunsaker, L. A., Gonzales, A. M., Heynekamp, J. J., Orlando, R. A., Deck, L. M. and Vander Jagt, D. L. (2006) TPA-induced up-regulation of activator protein-1 can be inhibited or enhanced by analogs of the natural product curcumin. *Biochem. Pharmacol.* 72, 928-940.
90. Witz, G. (1989). Biological interactions of α,β-unsaturated aldehydes. *Free Rad. Biol. Med.* 7, 333-349.
91. Zhang, L., Gavin, T., Geohagen, B. C., Liu, Q., Downey, K. J. and LoPachin, R. M. (2013). Protective properties of 2-acetylcyclopentanone in a mouse model of acetaminophen hepatotoxicity. *J. Pharmcol. Exp. Ther.* 346, 259-269.
92. Zwingmann C and Bilodeau M (2006) Metabolic insight into the hepatoprotective role of N-acetylcysteine in mouse liver. *Hepatology* 43, 454-463.
93. Firouzabdi, H., Iranpoor, N., Armani, K. (2002) Heteropoly Acids as Heterogeneous Catalysts for Thioacetalization and Transthioacetalization Reactions. *Synthesis,* 59-62.
94. Ben Mosbah I, Rosello-Catafau J, Alfany-Fernandez I, Rimola A et al. (2010) Addition of carvedilol to University of Wisconsin solution improves rat steatotic and nonsteatotic liver preservation. *Liver Transplant* 16: 163-171.
95. Jaeschke H, Woolbright B L (2012) Current strategies to minimize hepatic ischemia-reperfusion injury by targeting reactive oxygen species. *Transplant Rev* 26: 102-114.
96. Klune J R, Tsung A (2010) Molecular biology of liver ischemia/reperfusion injury: established mechanisms and recent advancements. *Surg Clin North Am* 90: 665-677.
97. Muhlbacher F, Langer F, Mittermayer C (1999) *Transplant Proc.* 31: 2069-2070.

What is claimed is:

1. A method of reducing the incidence of or treating electrophilic hepatotoxicity due to a therapeutic agent that can cause electrophilic metabolite hepatotoxicity in a subject receiving the therapeutic agent comprising administering to the subject a compound of formula (I) in an amount effective to scavenge the electrophilic metabolite and reduce the incidence of or reduce electrophilic hepatotoxicity due to the therapeutic agent, wherein the compound has the structure:

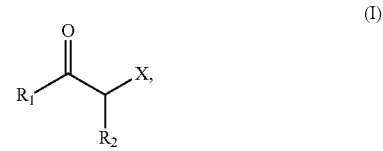

wherein
  $R_1$ and $R_2$ are independently H or alkyl or form a 5- or 6-membered ring that optionally contains one or more O, S, N or substituted N, where substitution at N is an alkyl or acyl group;
  X is $COR_3$;
  $R_3$ is H, alkyl, alkoxy alkyl, acyloxy alkyl, aryl, aryloxy, acyloxy aryl, cyclic, polycyclic, heterocyclic, heteroaryl, heteroaryloxy, acyloxy heteroaryl, or trifluoromethyl;
  wherein any alkyl can independently be branched or unbranched;
  wherein any aryl or heteroaryl can independently be optionally substituted with one or more —CH3, —NH2, —OH, =O, halogen, alkyl, alkoxy, acyloxy, aryl and/or acyloxyaryl;
  or a tautomer thereof; or a geometric or optical isomer thereof; or racemate thereof;
  or a pharmaceutically acceptable salt thereof,
  wherein the electrophilic metabolite is a soft electrophilic metabolite, an unsaturated carbonyl derivative, an unsaturated aldehyde derivative, N-acetyl-p-benzoquinone imine (NAPQI), p-benzoquinone, or combinations thereof.

2. The method of claim 1, wherein the therapeutic agent is acetaminophen, diclofenac, cyclophosphamide, valproic acid, clopidogrel, esomeprazole, cisplatin, a platinum containing antineoplastic agent, or radiation used in radiation therapy.

3. The method of claim 1, wherein the compound is administered to the subject at the same time that the therapeutic agent is administered to the subject.

4. The method of claim 3, wherein the compound and the therapeutic agent are administered in the same formulation.

5. The method of claim 1, wherein the compound is administered to the subject before the therapeutic agent is administered to the subject or wherein the compound is administered to the subject after the therapeutic agent is administered to the subject.

6. The method of claim 1, wherein the compound is administered by parenteral administration or wherein the compound is formulated with an enteric coating and the compound is administered by oral administration.

7. The method of claim 1, wherein the compound has the structure

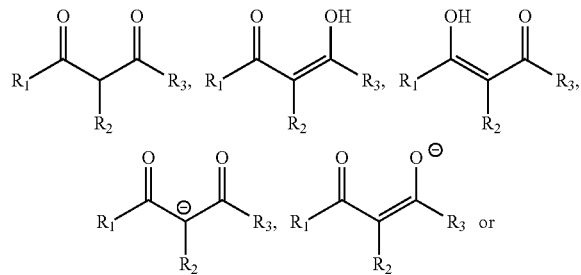

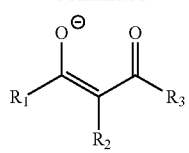

or a pharmaceutically acceptable salt thereof.

8. The method of claim 1, wherein any alkyl is independently C1-C6 alkyl.

9. The method of claim 1, wherein any alkyl is independently C1-C3 alkyl.

10. The method of claim 1, wherein the compound has the structure:

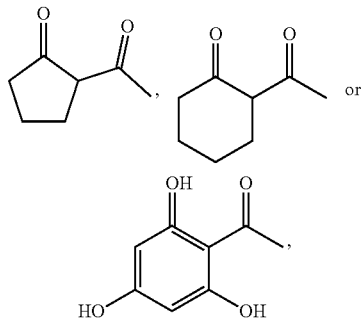

or a tautomer thereof; or a pharmaceutically acceptable salt thereof.

* * * * *